United States Patent [19]

Hoshi et al.

[11] Patent Number: 4,591,641
[45] Date of Patent: May 27, 1986

[54] SUBSTITUTED VINYL CEPHALOSPORINS

[75] Inventors: Hideaki Hoshi, Ichikawa; Jun Okumura, Yokohama; Takayuki Naito, Kawasaki; Yoshio Abe; Shimpei Aburaki, both of Tokyo, all of Japan

[73] Assignee: Bristol-Myers Company, New York, N.Y.

[21] Appl. No.: 713,207

[22] Filed: Mar. 18, 1985

Related U.S. Application Data

[60] Division of Ser. No. 564,604, Dec. 28, 1983, Pat. No. 4,520,022, which is a continuation-in-part of Ser. No. 461,833, Jan. 28, 1983, abandoned.

[51] Int. Cl.$^4$ ............... C07D 501/22; A61K 31/545
[52] U.S. Cl. ............................... 544/16; 544/30
[58] Field of Search ............ 544/16, 21, 30; 514/200, 209

[56] References Cited

U.S. PATENT DOCUMENTS

| | | |
|---|---|---|
| 3,351,596 | 11/1967 | Chamberlin . |
| 3,485,819 | 12/1969 | Weisenborn et al. . |
| 3,489,751 | 1/1970 | Crast, Jr. . |
| 3,489,752 | 1/1970 | Crast, Jr. . |
| 3,507,861 | 4/1970 | Morin et al. . |
| 3,769,277 | 10/1973 | Long et al. . |
| 3,830,700 | 8/1974 | O'Callaghan et al. . |
| 3,925,372 | 12/1975 | Chauvette . |
| 3,983,113 | 9/1976 | Beeby . |
| 3,994,884 | 11/1976 | Weir . |
| 4,049,806 | 9/1977 | Beeby . |
| 4,065,620 | 12/1977 | Webber . |
| 4,094,978 | 6/1978 | Beeby . |
| 4,107,431 | 8/1978 | Clark et al. . |
| 4,112,087 | 9/1978 | Beeby . |
| 4,139,618 | 2/1979 | Beeby . |
| 4,147,863 | 4/1979 | Miyadera et al. . |
| 4,255,423 | 3/1981 | Beattie et al. . |
| 4,307,230 | 12/1981 | Farge et al. . |
| 4,520,022 | 5/1985 | Hoshi et al. ............ 514/200 |

FOREIGN PATENT DOCUMENTS

| | | |
|---|---|---|
| 0030630 | 6/1981 | European Pat. Off. . |
| 3019445 | 12/1980 | Fed. Rep. of Germany . |
| 2264019 | 10/1975 | France . |
| 2264021 | 10/1975 | France . |
| 1341712 | 12/1973 | United Kingdom . |
| 1342241 | 1/1974 | United Kingdom . |
| 1472174 | 5/1977 | United Kingdom . |

OTHER PUBLICATIONS

J. Med. Chem. 18(10) 986–992 (1975), Webber et al.

*Primary Examiner*—Nicholas S. Rizzo
*Attorney, Agent, or Firm*—Robert E. Carnahan

[57] ABSTRACT

3-[(Z)-1-Propen-1-yl]-7-acylamido cephalosporins in which the 7-acyl group is phenylglycyl or substituted phenylglycyl are orally active antibiotics against Gram+ and Gram− bacteria.

4 Claims, No Drawings ial
SUBSTITUTED VINYL CEPHALOSPORINS

REFERENCE TO RELATED APPLICATIONS

This application is a divisional of copending application Ser. No. 564,604 filed Dec. 28, 1983 now U.S. Pat. No. 4,520,022 which in turn was a continuation-in-part of Ser. No. 461,833 filed Jan. 28, 1983 and now abandoned.

FIELD OF THE INVENTION

The present invention relates to a selection of cephalosporin compounds having the 3-((Z)-1-propenyl) and 7-phenylglycylamido groups, the latter may be substituted, (Class 544, Subclass 16) and to methods of treating bacterial infections employing these compounds (Class 424, Subclass 246).

DESCRIPTION OF THE PRIOR ART

The 3-formylceph-3-em compounds used as intermediates in one method of preparation of the 3-substituted vinyl cephalosporins of the present invention may be prepared by oxidation of the corresponding 3-hydroxymethylceph-3-ems obtained by enzymatic hydrolysis of the corresponding cephalosporins. This process is represented in the prior art by Chamberlin, U.S. Pat. No. 3,351,596 (Nov. 7, 1967) who disclosed inter alia Compounds II, and III.

[Structure I: RCONH-ceph-3-CHO with CO₂CH₃]

R = [thienylmethyl] and [phenylglycyl CH(NH₂)]

II   III

Chamberlin (loc. cit.) disclosed derivatives at the 3—CHO group with carbonyl reagents such as semicarbazide and hydroxylamine, but there was no disclosure of any carbon alkylation of the 3—CHO.

The corresponding sulfoxides are more stable and can be prepared in better yield (Webber, U.K. patent specification No. 1,341,712, published December 23, 1973).

The first disclosure of 3-alkenyl substituted cephalosporins was by Clark et al. in U.K. patent specification No. 1,342,241, published Jan. 3, 1974 (corresponding U.S. Pat. Nos. 3,769,277, and 3,994,884, granted Oct. 30, 1973, and Nov. 30, 1976). The Compounds IV and V are disclosed on pp. 25 and 29 of the U.K. Specification.

[Structure IV: phenylglycyl-ceph-CH=CH₂]

[Structure V: thienylmethyl-CH₂CONH-ceph-CH=CHCH₃]

These compounds were prepared by reacting the corresponding 3-triphenylphosphoniummethyl cephalosporin with formaldehyde or acetaldehyde. The inverse process of reacting a phosphoranylidine derivative of the formula $R_3P=CR^3R^4$ with a 3—CHO cephalosporin is also disclosed in the specification on page 5. Compound IV is stated to be absorbed when given by the oral route in U.S. Pat. No. 4,107,431.

Another early disclosure of compounds of this type was by Webber et al. J. Med. Chem. 18(10) 986–992, (1975), and in U.S. Pat. No. 4,065,620 patented Dec. 27, 1977 which discloses at columns 3, 4, and 5 the genus to which the present compounds belong. Specific compounds disclosed are represented by Formula VI.

[Structure VI: phenylglycyl-ceph-CH=CHCO₂H (CO₂Et) (CN)]

Other variations of this type are disclosed in U.S. Pat. Nos. 4,094,978 (June 13, 1978), and 4,112,087 (Sept. 5, 1978) where Compounds VII and VIII are disclosed.

[Structure VII: HO-phenyl-CHCONH-ceph-CH=CHCH₂OH]
U.S. Pat. No. 4,094,978 Col. 44

[Structure VIII: HO-phenyl-CHCONH-ceph-CH=CHCH₂OCH₃ (trans)]
U.S. Pat. No. 4,112,087 Col. 31

Other substituted 3-alkenyl cephalosporins are disclosed in the following patent publications.

U.S. Pat. No. 3,830,700, O'Callaghan et al. (April 20, 1974) 3-(nitrostyryl)cephalexin analogs U.S. Pat. No. 3,983,113, Beeby (Sept. 28, 1976), U.S. Pat. No. 4,049,806, Beeby (Sept. 20, 1977), and U.S. Pat. No. 4,139,618, Beeby (Feb. 13, 1979), 3-(heterocyclothio)propenyl cephalosporins U.S. Pat. No. 4,147,863, Miyadera et al. (Apr. 3, 1979), 3-(1-methyl-5-tetrazolyl)vinyl cephalosporins Ger. Offen. No. DE 3019445 (December, 1980) 3-(sulfonyloxy)vinyl cephalosporins Fr. No. 2460302 (Jan. 23, 1981) 3-(dimethylamino)vinyl cephalexin analogs Eu No. 30630 (June 24, 1981) 7-[(3-methanesulfonamidophenyl)-α-aminoacetamido]-3-vinylceph-3-em-4-carboxylic acid U.S. Pat. No. 4,255,423, Beattie et al. (Mar. 10, 1981)

U.S. Pat. No. 4,390,693, Beattie et al. (June 28, 1983) 7-(2-thienyl)acetamido-3-(3-acetoxy-1-propenyl) and -3-(heterocyclovinyl)ceph-3-em-4-carboxylic acids, and 7α-methoxy analogs.

The principal commercially available orally active cephalosporins, the use for which the present compounds are intended, are cephalexin, cefadroxil, cephradine, and cefaclor. These substances have Formulas IX, X, XI, and XII.

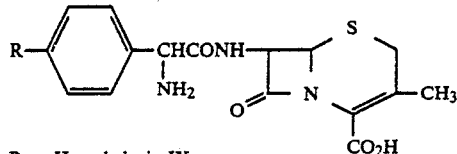

R = H cephalexin IX
R = OH cefadroxil X

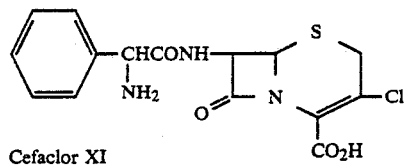

Cefaclor XI

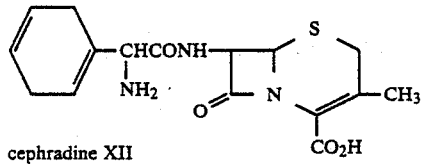

cephradine XII

These compounds are the subjects of the following patents.

cephalexin—U.S. Pat. No. 3,507,861 (Apr. 21, 1970)
cefadroxil—U.S. Pat. No. 3,489,752 (Jan. 13, 1970) (U.S. Pat. No. Re 29,164)
cefaclor—U.S. Pat. No. 3,925,372 (Dec. 9, 1975)
cephradine—U.S. Pat. No. 3,485,819 (Dec. 23, 1969)

Related structures which have been disclosed are 3-chlorocefadroxil and 3-hydroxycefadroxil respectively in U.S. Pat. No. 3,489,751 (Jan. 13, 1970) and U.K. Specification No. 1,472,174 (published May 4, 1977).

SUMMARY OF THE INVENTION

The present invention provides compounds of Formulas XIII, and XIV

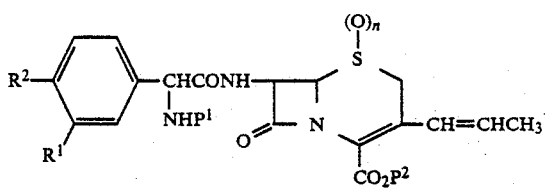

Formula XIII

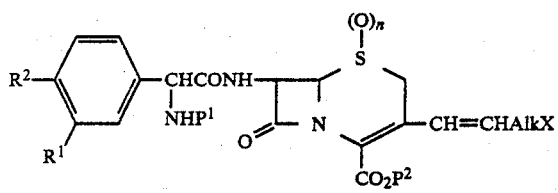

Formula XIV

In these formulas:

n is the integer 0, or 1, $R^1$ is hydrogen, $OP^3$, lower alkoxy, or halogen including chlorine, bromine, fluorine, and iodine, $P^1$, $P^2$, and $P^3$ are hydrogen atoms or conventional protecting groups used in cephalosporin chemistry respectively with amino, carboxy, and hydroxy groups, $R^2$ is hydrogen, $OP^3$, or lower alkoxy Alk is an alkylidene or alkylene group having from 1 to 4 carbon atoms, and X is chlorine, bromine, or iodine.

Those compounds wherein n is 1, and $P^1$, $P^2$, and $P^3$ are conventional protecting groups, are intermediates for making the biologically active end products of the present invention which are represented by Formula XIII when n is 0, and $P^1$, $P^2$, and $P^3$ are hydrogen. These products are of interest as orally effective cephalosporin antibiotics having strong activity against Gram-positive bacteria and an improved spectrum of activity against Gram-negative bacteria, various fastidious bacteria, and anaerobes relative to cephalexin, cefadroxil, cefaclor, and cephradine. They provide prolonged antibiotic concentrations in the blood stream following oral administration and are suitable for administration to humans on a once or twice a day basis. As such they are administered in doses ranging from 100 mg. to 5,000 mg. per day depending upon the size of the patient and the disease condition. They may be administered parenterally in similar dosage amounts.

The products of Formula XIV are of interest chiefly as intermediates. Those, however, wherein n is 0, and $P^1$, $P^2$, and $P^3$ are hydrogen possess antibacterial activity and are also useful as antibiotics.

In view of these properties, the compounds of Formula XIII and Formula XIV wherein n is 0, and $P^1$, $P^2$, and $P^3$ are hydrogen are useful for the treatment of bacterial infections caused by sensitive organisms in mammals. For this purpose they are administered orally or parenterally in antibacterially effective non-toxic doses as such or in the form of one of their pharmaceutically acceptable acid addition salts, pharmaceutically acceptable metal or amine salts, or as a pharmaceutically acceptable ester.

The pharmaceutically acceptable acid addition salts are those in which the anion does not contribute significantly to the toxicity of the salt and which salts are compatible with the customary pharmaceutical vehicles and adapted for oral or parenteral administration. They include the salts of Formulas XIII and XIV wherein n=0, and $P^1$ is hydrogen with mineral acids such as hydrochloric acid, hydrobromic acid, phosphoric acid, and sulfuric acid, with organic carboxylic acids or organic sulfonic acids such as acetic acid, citric acid, maleic acid, succinic acid, benzoic acid, tartaric acid, fumaric acid, mandelic acid, ascorbic acid, malic acid, methanesulfonic acid, p-toluenesulfonic acid, and other acids known and used in the penicillin and cephalosporin arts. Preparation of these salts is carried out by conventional techniques involving reaction of one of the substances of Formulas XIII or XIV wherein n is 0 and $P^1$ is hydrogen with the acid in a substantially equivalent amount.

Pharmaceutically acceptable metal and amine salts similarly are those salts of the compounds of Formulas XIII and XIV wherein n is 0 and $P^2$ is hydrogen which are stable under ambient conditions, and in which the cation does not contribute significantly to the toxicity or biological activity of the salt. Suitable metal salts include the sodium, potassium, barium, zinc, and aluminum salts. The sodium or potassium salts are preferred. Amine salts prepared from amines used for instance with benzyl penicillin which are capable of forming stable salts with the acidic carboxyl group include trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, and dicyclohexylamine.

Pharmaceutically acceptable esters include those esters which are active per se, or which serve as prodrugs by being hydrolyzed in the body to yield the antibiotic per se. Suitable esters of the latter type are the phenacyl, acetoxymethyl, pivaloyloxymethyl, α-acetoxyethyl, α-acetoxybenzyl, α-pivaloyloxyethyl, 3-phthalidyl, 5-indanyl, methoxymethyl, benzoyloxymethyl, α-ethylbutyryloxymethyl, propionyloxymethyl, valeryloxymethyl, isobutyryloxymethyl, glycyloxymethyl, and others known in the penicillin and cephalosporin arts.

The compounds of Formulas XIII and XIV wherein n is 0, and $P^1$, $P^2$, and $P^3$ are hydrogen atoms and their salts as defined above may be formulated for oral or parenteral use in conventional manner using known pharmaceutical carriers and excipients, and they may be presented in unit dose form or in multiple dose containers. The compositions may be in the form of tablets, capsules, solutions, suspensions, or emulsions. These compounds may also be formulated as suppositories utilizing conventional suppository bases such as cocoa butter or other fatty materials. The compounds may, if desired, be administered in combination with other antibiotics including cephalosporins, penicillins, and aminoglycosides.

DETAILED DESCRIPTION OF THE INVENTION

Table 1 contains a summary of the structures of the products disclosed in Procedures 1–43. Most of these compounds are 7β-(D-phenylglycylamido)cephalosporins having the 1-propen-1-yl group in the 3-position. The terminal carbon atom of the propenyl substituent of some of them bears a substituent such as an alkyl group (methyl), halogen (chlorine or iodine), an aryl group (phenyl), a hetrocyclothio group (1,2,3-triazol-5-yl thio), or an alkoxy group (methoxy). The phenylglycylamido group may be unsubstituted, or mono, or disubstituted by hydroxy, alkoxy, or halogen.

TABLE 1
Products Disclosed in Procedures 1–43

| Compound No. | $R^1$ | $R^2$ | $R^3$ | (configuration) |
|---|---|---|---|---|
| 9 (BMY-28100) | H | OH | —CH$_3$ | (Z) |
| 13 (BBS-1058) | H | OH | —C$_2$H$_5$ | (Z) |
| 11 (BBS-1064) | H | OH | —H | — |
| 24 (BBS-1065) | H | H | —CH$_3$ | (Z) |
| 26 (BBS-1066) | H | H | —CH$_2$Cl | (Z) |
| 8 (BBS-1067) | H | OH | —CH$_3$ | (E) |
| 15 (BBS-1076) | H | OH | —CH$_2$C$_6$H$_5$ | (Z) |
| 21 (BBS-1091) | H | OH | —CH$_2$—S—(triazole) | |
| 17 (BBS-1092) | H | OH | —CH$_2$OCH$_3$ | (Z) |
| 32 (BMY-28060) | Cl | OH | —CH$_3$ | (Z) |
| 37 (BMY-28068) | HO | OH | —CH$_3$ | (Z) |
| 42 (BMY-28097) | CH$_3$O | OH | —CH$_3$ | (Z) |

Table 2 provides a summary of the in vitro antibacterial activity of the substances disclosed in the present specification Minimum inhibitory concentrations determined by the agar dilution technique for three groups of organisms designated Gp-Ia, Gp-Ib, and Gn-Ia are provided. Each of these groups of organisms is constituted of five individual strains of microorganism which are identified in a footnote to the table. The Gp-Ia organisms are Gram+ staphylococci which are sensitive to penicillin. The Gp-Ib organisms are Gram+ staphylococci which are resistant to penicillin and produce penicillinase. The Gn-Ia organisms are Gram− bacteria which are sensitive to ampicillin and cephalothin. The present substances have generally low activity against ampicillin and cephalothin resistant Gram− bacteria. The following conclusions can be drawn from Table 2 concerning the in vitro antibacterial activity of these compounds.

All of the compounds have good activity against penicillin sensitive staphylococci (Gp-Ia). They are generally less active against the penicillin resistant staphylococci (Gp-Ib) by a factor of three or more. In each instance, however, the compounds are several fold more active than cephalexin and cefadroxil.

Only those compounds having the unsubstituted cis(Z)-propenyl group in the 3-position have good activity against the Gram− bacteria (Gn-Ia). Refer to Compound Nos. 9, 24, 32, and 42. The trans(E)-propenyl compound, Compound No. 8, is less active against the Gram− bacteria by a factor of 8 relative to the corresponding cis-propenyl compound, Compound No. 9. Similarly, substitution on the terminal methyl group of the propenyl substituent in the 3-position appears to result in a reduction of Gram− activity. Refer to Compound Nos. 13, 15, 21, and 17. This is true of the vinyl compound also, No. 11. These compounds are nevertheless potent antibacterial agents being substantially equivalent to cephalexin and cefadroxil. Ring substitution is in no way detrimental to antibacterial activity. Compare Compound Nos. 9, 24, 32, and 42. Compound No. 37 appears to be an exception to each of the foregoing conclusions, but in fact, it is an highly active substance against both of the Gram+ and Gram− bacteria as will be shown in Table 3.

TABLE 2

Agar Dilution Technique (Mueller-Hinton Agar)
Minimum Inhibitory Concentration (mcg/ml)

| Compound No. | Gp Ia[3] 1 | 2 | Gp Ib[3] 1 | 2 | Gn Ia[3] 1 | 2 |
|---|---|---|---|---|---|---|
| 9 (BMY-28100) | 0.23 | 0.35 | 0.92 | 0.8 | 0.8 | 0.7 |
| 13 (BBS-1058) | 0.40 | | 1.4 | | 4.1 | |
| 11 (BBS-1064) | 0.40 | | 1.2 | | 3.6 | |
| 24 (BBS-1065) | 0.23 | 0.3 | 0.92 | 0.92 | 0.8 | 0.8 |
| 8 (BBS-1067) | 0.26 | | 1.4 | | 6.3 | |
| 15 (BBS-1076) | 0.20 | | 0.7 | | >50 | |
| 21 (BBS-1091) | 0.61 | | 2.7 | | 2.7 | |
| 17 (BBS-1092) | 0.53 | | 2.1 | | 2.7 | |
| 32 (BMY-28060) | | 0.13 | | 0.53 | | 1.1 |
| 37 (BMY-28068) | | 6.30 | | 7.2 | | 6.3 |
| 42 (BMY-28097) | 0.35[4] | | 1.2[4] | | 0.53[4] | |
| cephalexin | 1.2 | 0.70 | 4.1 | 3.6 | 6.2 | 4.1 |
| Cefadroxil | 1.2 | 1.10 | 3.6 | 4.1 | 8.3 | 8.3 |

[1]Columns 1 and 2 report separate test runs.
[2]Columns 1 and 2 report separate test runs.
[3]Average of five organisms each group - Gp Ia Gram+ *staphylococci*; penicillin sensitive; no penicillinase produced.
*S. aureus* Smith A9537
*S. aureus* A9497
*S. aureus* Terajima
*S. aureus* A9534
*S. aureus* A9601
Gp Ib Gram+ *staphylococci*; penicillin resistant; penicillinase producers.
*S. aureus* 193
*S. aureus* BX-1633-2 A9606
*S. aureus* A15092
*S. aureus* Russell
*S. aureus* A9602
Gn Ia Gram− bacteria; ampicilin and cephalothin sensitive.
*E. coli* Juhl A15119
*E. coli* A9660
*K. pneumoniae* D11
*P. mirabilis* A9554
*P. mirabilis* A9900
[4]Not part of run 1; tested separately.

Table 3 contains comparative data for in vitro antibacterial activity against the same organisms as in Table 2 employing two different bacteriological culture media. Mueller-Hinton agar is the standard medium employed in the tests referred to in Table 2. Table 3 contains a comparison of the minimum inhibitory concentrations of three of the test compounds determined first in Mueller-Hinton medium and then in nutrient agar. Compound No. 9 which contains 4-hydroxy sustitution in the phenyl ring and Compound No. 42 which contains the 3-methoxy-4-hydroxy substitution in the phenyl ring reflect only a moderate medium effect. By this it is meant that the differences in MIC are less than three fold. Compound No. 37, the 3,4-dihydroxyphenyl substituted compound reflects differences in activity between the two media of from 6 to 12 fold, the minimum inhibitory concentrations in nutrient agar being much lower than those determined Mueller-Hinton agar. Accordingly, Compound No. 37 was concluded to be comparable in antibacterial effect to the other cephalosporins having the cis-propenyl group in the 3-position which are referred to in Table 2. This phenomenon whereby an antibiotic shows greater activity in one type of nutrient medium than in another has been reported and studied previously. Refer to T. A. Pursiano et al. Antimicrobial Agents and Chemotherapy, Vol. 3, No. 1, pp. 33–39 (1973).

TABLE 3

Test Medium Comparison
Agar Dilution Technique
Minimum inhibitory Concentration (mcg/ml)

| Compound No. | | Gp Ia[2] | Gp Ib[2] | Gn Ia[2] |
|---|---|---|---|---|
| 9 (BMY-28100) | A[1] | 0.23 | 0.92 | 0.70 |
| | B | 0.17 | 0.35 | 0.70 |
| 37 (BMY-28068) | A | 4.8 | 6.3 | 5.5 |
| | B | 0.40 | 0.61 | 0.92 |
| 42 (BMY-28097) | A | 0.35 | 1.2 | 0.53 |
| | B | 0.23 | 0.40 | 0.40 |

[1]A Mueller-Hinton agar
B Nutrient agar
[2]Average values for the same groups of organisms as in Table 2

The structure activity correlations drawn from the foregoing in vitro studies are born out by the results of in vivo studies in mice. Table 4 is a tabulation of the protective doses for mice infected with a lethal inoculum of a bacteria. Two different bacteria were employed in the studies, one a Gram+ organism and the other a Gram− organism. The protective dose ($PD_{50}$) is that dose which when administered to a group of infected mice results in 50% survival after five days. Normally untreated infected mice die within three days following injection of the lethal inoculum.

TABLE 4

Protective Dose for Mice Infected with Lethal Inoculum[1]
Oral Treatment

| Compound No. | *S. aureus* Smith | *E. coli* Juhl |
|---|---|---|
| 9 (BMY-28100) | 0.14 (0.31)[2] | 1.2 (8.4)[2] |
| 13 (BBS-1058) | 0.32 (0.31) | 3.0 (8.4) |
| 11 (BBS-1064) | 0.18 (0.31) | 3.8 (8.4) |
| 34 (BBS-1065) | 0.18 (0.27) | 1.5 (8.2) |
| 8 (BBS-1067) | 0.20 (0.31) | 7.5 (8.2) |
| 32 (BMY-28060) | 0.17 (0.22) | 3.04 (8.4) |
| 37 (BMY-28068) | 0.13 (0.27) | 0.44 (8.2) |
| 42 (BMY-28097) | 0.09[3] | |

[1]Dose in mg/kg. preventing death for 5 days in 50% of the animals in groups of 5 mice treated with various doses of the test compound on the day of infection; determined by interpolation from the dose/response curve; untreated animals die within 3 days.
[2]Values in parentheses are for cephalexin in the same run.
[3]In this run a value of 0.16 mg/kg. was obtained for BMY-28100; control values for cephalexin or cefadroxil not available.

The data in Table 4 are drawn from several different experiments. In these experiments cephalexin was used as a control treatment. The $PD_{50}$ value determined for cephalexin in the same experiment is given in parentheses next to the $PD_{50}$ values of the test compounds. It is evident that each of the cephalosporins possesses good activity against the Gram+ *Staphylococcus aureus* infection, and that the compounds bearing the cis propenyl group in the 3-position are more active against the Gram− infection, Compounds 9, 24, and 37.

Table 5 contains comparative blood-level data for mice treated orally and intramuscularly with the test compounds listed in Table 1. Uniformly good oral absorption is reflected except for Compound No. 21 which bears a heterocyclothio substituent on the 3-propenyl group. Compound No. 37 exhibits exceptionally high blood levels in the mouse following oral administration. This compound has been shown to be metabolized in the rat to Compound No. 42. Refer to Procedure 43. Compound No. 37 is the 3,4-dihydroxyphenyl compound and Compound No. 42 is the 3-methoxy-4-hydroxyphenyl compound. The latter has been shown to have high in vitro and in vivo activity.

TABLE 5

| | Mouse blood levels Dose: | | | | | | | | |
|---|---|---|---|---|---|---|---|---|---|
| | 100 mg/kg, p.o. | | | 20 mg/kg, p.o. | | | 20 mg/kg, i.m. | | |
| Compound No. | $C_{max}$ (mcg/ml) | $T_{\frac{1}{2}}$ (hr) | AUC (mcg·hr/ml) | $C_{max}$ (mcg/ml) | $T_{\frac{1}{2}}$ (hr) | AUC* (mcg·hr/ml) | $C_{max}$ (mcg/ml) | $T_{\frac{1}{2}}$ (hr) | AUC* (mcg·hr/ml) |
| Run 1 | | | | | | | | | |
| 9 (BMY-28100) (lot 2) | 56 | 1.9 | 106 | 15 | 1.9 | 26 | 28 | 0.88 | 32 |
| 13 (BBS-1058) | 51 | 1.9 | 150 | 13 | 2.0 | 41 | 25 | 0.74 | 20 |
| 11 (BBS-1064) | 43 | 1.2 | 49 | 11 | 1.4 | 13 | 23 | 0.37 | 15 |
| 24 (BBS-1065) | 40 | 1.1 | 84 | 7.8 | 1.3 | 15 | 31 | 0.50 | 22 |
| 8 (BBS-1067) | 30 | 1.4 | 69 | 10 | 1.3 | 22 | 31 | 0.63 | 31 |
| 15 (BBS-1076) | 41 | 2.7 | 81 | 12 | 2.7 | 38 | 31 | 0.99 | 52 |
| 21 (BBS-1091) | 4.4 | 3.2 | 19 | 1.7 | 2.6 | 6.6 | 16 | 0.54 | 9.6 |
| 17 (BBS-1092) | 73 | 1.7 | 197 | 18 | 1.6 | 28 | 24 | 0.60 | 19 |
| Cephalexin* | 47 | 1.4 | 57 | 11 | 1.3 | 14 | 26 | 0.40 | 16 |
| Cefadroxil | 56 | 2.3 | 103 | 12 | 1.2 | 18 | 21 | 0.33 | 14 |
| Run 2 | | | | | | | | | |
| 9 (BMY-28100) | 61 | 1.3 | 86 | 15 | 1.7 | 13 | 21 | 0.48 | 13 |
| 24 (BBS-1065) | 33 | 1.1 | 46 | 9.5 | 0.69 | 13 | 16 | 0.58 | 13 |
| 32 (BMY-28060) | 25 | 1.7 | 37 | 7.9 | 1.7 | 13 | 21 | 0.48 | 13 |
| 37 (BMY-28068) | 180 | 2.5 | 666 | 58 | 5.1 | 270 | 86 | 1.2 | 233 |
| Cefadroxil | 51 | 1.5 | 67 | 18 | 1.6 | 21 | 30 | 0.37 | 21 |

*Mean of 3 runs.

Table 6 contains additional in vivo data for Compound No. 9 against four other organisms compared to cephalexin, cefachlor, and cefadroxil. Tables 7 and 8 contain comparative in vitro data for Compound No. 9 versus cephalexin, cefadroxil, and cefachlor with respect to a number of Streptococci, Neisseria, Haemophilis, and various anerobes.

In rat urinary recovery experiments, the 24 hour recovery of Compound No. 9 from the urine of rats treated orally is comparable to that of cephalexin and cefadroxil, and greater than that of cefachlor. Stability studies comparing Compound No. 9 with cephalexin and cefachlor in solution using phosphate buffer at pH 6.5 and pH 7.0, human serum (pH 6.8), horse serum (pH 7.6), and calf serum (pH 8.2) as vehicles has revealed that Compound No. 9 is remarkably more stable than cefachlor and comparable to cephalexin.

TABLE 6

Protective Dose $PD_{50}$ for Mice Infected with Lethal Inoculum Oral Treatment

| Organism | 9 (BMY-28100) | Cephalexin | Cefachlor | Cefadroxil |
|---|---|---|---|---|
| S. aureus BX-1633 | 2.2 | 17 | 2.2 | 7.2 |
| S. pyogenes A20201 | 0.11 | 0.74 | 0.14 | 0.23 |
| H. influenza A9729 | 1.8 | 18 | 1.6 | 25 |
| P. mirabilis A9554 | 1.8 | 12.5 | 1.8 | 14 |

TABLE 7

In Vitro Activity Against Streptococci, Neisseria, and Haemophilis

| | | MIC (mcg/ml) | | | | |
|---|---|---|---|---|---|---|
| Organism | | 9 (BMY-28100) (lot 2) | 15 (BBS-1076) | Cephalexin | Cefadroxil | Cefaclor |
| S. pyogenes S-23 | | 0.05 | 0.2 | 0.8 | 0.8 | 0.2 |
| S. pyogenes Dick | | 0.05 | 0.2 | 0.8 | 0.8 | 0.2 |
| S. pyogenes | A9604 | 0.05 | 0.2 | 0.8 | 0.8 | 0.2 |
| S. pyogenes | A20065 | 0.05 | 0.2 | 0.8 | 0.8 | 0.2 |
| S. pyogenes | A15040 | 0.05 | 0.2 | 0.8 | 0.8 | 0.2 |
| Geometric Mean | | 0.050 | 0.20 | 0.80 | 0.80 | 0.2 |
| S. pneumoniae Type II | | 0.2 | 0.2 | 3.1 | 1.6 | 1.6 |
| S. pneumoniae Type I | | 0.2 | 0.2 | 3.1 | 1.6 | 1.6 |
| S. pneumoniae Type III | | 0.2 | 0.2 | 3.1 | 1.6 | — |
| S. pneumoniae | A9585 | 0.2 | 0.4 | 3.1 | 1.6 | 1.6 |
| S. pneumoniae | A15069 | 0.2 | 0.2 | 3.1 | 1.6 | 0.8 |
| Geometric Mean | | 0.20 | 0.23 | 3.1 | 1.6 | 1.3 |
| N. gonorrheae | A15112 | 0.8 | >100 | 6.3 | 6.3 | 0.8 |
| N. gonorrheae | A20142 | 0.8 | >100 | 6.3 | 6.3 | — |
| N. gonorrheae | A20143 | 0.8 | >100 | 6.3 | 6.3 | 0.8 |
| N. gonorrheae | A20154 | 0.8 | >100 | 6.3 | 6.3 | 0.8 |
| N. gonorrheae | A20155 | 0.8 | >100 | 6.3 | 6.3 | 0.8 |
| Geometric Mean | | 0.80 | >100 | 6.3 | 6.3 | 0.8 |
| N. meningitidis | A20048 | 0.8 | >100 | 6.3 | 6.3 | 0.8 |
| N. meningitidis | A20049 | — | — | — | — | 0.8 |
| N. meningitidis | A21487 | 0.8 | >100 | 6.3 | 6.3 | 0.8 |
| N. meningitidis | A21496 | 0.8 | >100 | 6.3 | 6.3 | 0.8 |
| N. meningitidis | A21497 | 0.8 | >100 | 6.3 | 6.3 | 0.8 |
| Geometric Mean | | 0.80 | >100 | 6.3 | 6.3 | 0.8 |
| H. influenzae | A9729 | 0.8 | >100 | 6.3 | 6.3 | 0.8 |
| H. influenzae | A20177 | 0.8 | >100 | 6.3 | 6.3 | 0.8 |
| H. influenzae | A20193 | 0.8 | >100 | 6.3 | 6.3 | 0.8 |
| H. influenzae | A21523 | 0.8 | >100 | 6.3 | 6.3 | 0.8 |
| H. influenzae | A9033 | 0.8 | >100 | 6.3 | 6.3 | 0.8 |
| H. influenzae | A22483 | 0.8 | >100 | 6.3 | 6.3 | 0.8 |

TABLE 7-continued
In Vitro Activity Against Streptococci, Neisseria, and Haemophilis

| | | MIC (mcg/ml) | | | | |
|---|---|---|---|---|---|---|
| Organism | | 9 (BMY-28100) (lot 2) | 15 (BBS-1076) | Cephalexin | Cefadroxil | Cefaclor |
| H. influenzae | A22482 | 0.8 | >100 | 6.3 | 6.3 | 0.4 |
| Geometric Mean | | 0.80 | >100 | 6.3 | 6.3 | 0.66 |
| H. influenzae | A22157 | 1.6 | 25 | 3.1 | 6.3 | — |
| H. influenzae | A22481 | 1.6 | 25 | 3.1 | 6.3 | — |
| H. influenzae | A22491 | 1.6 | 25 | 3.1 | 6.3 | — |
| S. pyogenes | A20201 | 0.1 | 0.2 | 0.8 | 0.4 | — |
| S. pneumoniae | A20759 | 0.2 | 0.4 | 3.1 | 3.1 | — |

TABLE 8
In Vitro Activity Against Anaerobes

| | | Organism | β-Lactamase | MIC (mcg/ml) | | |
|---|---|---|---|---|---|---|
| | | | | 9 (BMY-28100) | Cephalexin | Cefaclor |
| Gn, rods | B. fragilis | A20928-1 | (−) | 0.8 | 12.5 | 3.1 |
| | " | A21900 | (−)* | 50 | 12.5 | 6.3 |
| | " | A20935 | (−) | 0.8 | 6.3 | 3.1 |
| | | Geometric Mean | | 3.2 | 9.9 | 3.9 |
| Gn, rods | B. fragilis | A22053 | (+) | 50 | 25 | 100 |
| | " | A22021 | (+) | >100 | 100 | >100 |
| | " | A22693 | (+) | >100 | >100 | >100 |
| | | Geometric Mean | | >100 | >75 | >100 |
| | " | A22695 | (+) | >100 | 100 | 100 |
| | " | A22533 | (+) | >100 | >100 | >100 |
| | | Geometric Mean | | >100 | >100 | >100 |
| Gp, rods | C. difficile | A21675 | * | 6.3 | 100 | 25 |
| | C. perfringens | A9645 | | 0.4 | 12.5 | 1.6 |
| Gp, cocci | P. acnes | A21933 | | 0.4 | 1.6 | 0.8 |
| | P. anaerobius | A21905 | | 0.8 | 6.3 | 0.4 |
| | | Geometric Mean | | 0.95 | 11 | |

*Clindamycin resistant

The compounds of the present invention are prepared by application of the synthetic routes disclosed in U.K. Specification No. 1,342,241, U.S. Pat. No. 3,994,884, and U.S. Pat. No. 4,107,431, which are cited above, to the appropriately selected starting materials. In essence, formation of the substituted vinyl group in the 3-position of the cephalosporins of the present invention involves reaction of a halide reactant with a triarylphosphine to yield a phosphonium salt which on treatment with base yields a phosphoranyl intermediate. The latter is then treated with a carbonyl reactant to produce the compound of the present invention. Either the halide reactant or the carbonyl reactant contains the cephalosporin nucleus. This is illustrated in the following reaction schemes.

In the foregoing reaction schemes, $R^3$ is H, $C_{1-4}$ alkyl, $C_{1-4}$ alkoxy-$C_{1-4}$-alkyl, $C_{7-14}$ aralkyl, or the group AlkX wherein Alk and X are as previously defined. The symbol Q refers to the 7-amino-3-cephem-3-yl-4-carboxylic acid nucleus wherein the amino and carboxylic acid groups may bear protecting groups such as the silyl group or other groups which are well-known to those skilled in the chemistry of the beta-lactam antibiotics, or Q may be a 7-acylamino-3-cephem-3-yl-4-carboxylic acid nucleus where the 7-acylamino group may be one which conventionally appears in cephalosporin antibiotics including the α-amino-α-substituted phenylacetamido group of the present invention as defined with respect to Formulas XIII and IX. The sulfox-

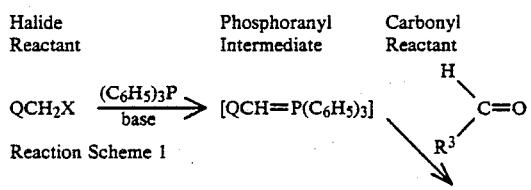

Reaction Scheme 1

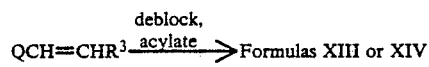

Reaction Scheme 2

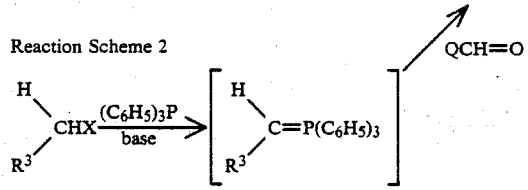

ides of the foregoing have advantages. Specifically, Q has one of the following formulas:

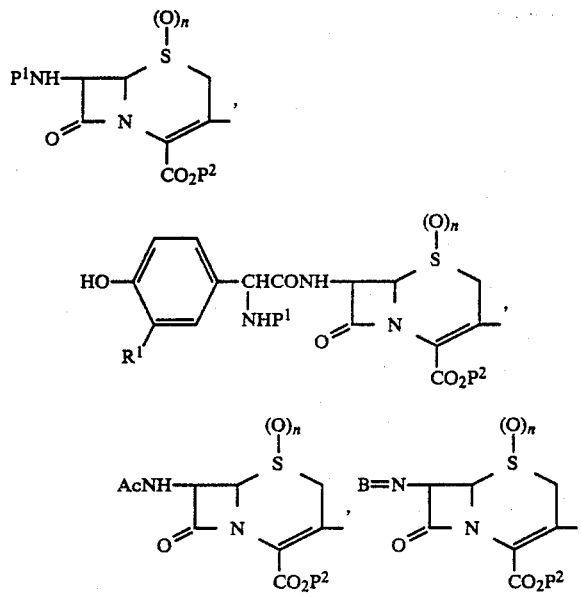

wherein:
$R^1$ has the same meaning as previously
n is the integer 0, or 1 referring to the number of oxygen atoms attached to sulfur,
Ac refers to an acyl group of the sort ordinarily found in the 7-acylaminocephalosporins such as phenylacetyl, phenoxyacetyl and
B is an alkylidene or aralkylidene protecting group derived from an aldehyde or ketone such as the benzylidene group which is easily removed at a subsequent stage for instance by hydrolysis using Girard's reagent T.
$P^1$, $P^2$, and $P^3$ are hydrogen atoms or protecting groups of the sort conventionally used in cephalosporin chemistry with amino groups, hydroxy groups, and the carboxyl group.

Suitable carbonyl protecting groups ($P^2$) include aralkyl groups such as benzyl, p-methoxybenzyl, p-nitrobenzyl, and diphenylmethyl(benzhydryl)alkyl groups such as t-butyl; haloalkyl groups such as 2,2,2-trichloroethyl, and other carboxyl protecting groups described in the literature, for instance, in British Specicification No. 1,399,086. We prefer to utilize carboxyl protecting groups which are readily removed by treatment with acid, particularly benzyhdryl or t-butyl.

Amino and hydroxy protecting groups ($P^1$ and $P^3$) are well-known in the art and include the trityl and acyl groups such as chloroacetyl, formyl, trichloroethoxycarbonyl, tert.-butoxycarbonyl, carbobenzyloxy, etc. Again amino protecting groups which are readily removed by treatment with acid are preferred, particularly the tert.-butoxycarbonyl group.

In Reaction Schemes 1 and 2 when cephalosporin nucleus Q is utilized in the form of the 1-oxide (n=1) the oxides are prepared by known procedures such as by oxidation of the corresponding cephalosporin (n=0) with m-chloroperbenzoic acid or peracetic acid. At some later stage in the synthesis the 1-oxide is reduced by known procedures, for example by reduction with iodide ion in an aqueous medium.

Conversion of the halide reactant of the formula $QCH_2X$ according to Scheme 1 to the phosphoranyl intermediate is preferably carried out employing a halide reactant wherein X is iodide. If a chloride or bromide halide reactant is used it may be first transformed into the iodide by treatment with sodium iodide in dimethylformamide or acetone solution. The iodide reactant readily reacts with a triarylphosphine such as triphenylphosphine in an organic liquid vehicle which in inert to the reactants under the reaction conditions. Room temperature for a brief period of up to several hours constitute suitable conditions. Suitable triarylphosphines in addition to triphenylphosphine include the readily available compounds having reaction compatible aryl groups such as substituted phenyl e.g. tolyl, naphthyl, substituted naphthyl, and heteroaromatic or substituted heteroaromatic groups. The first stage of the reaction involves formation of the triarylphosphonium salt which ordinarily precipitates from solution and is collected on a filter. The triarylphosphonium salt is then dissolved in a suitable liquid organic solvent which is water immiscible and inert under the reaction conditions such as chloroform, trichloroethylene, or other polychlorinated or brominated methane or ethane. The phosphoranyl intermediate is then produced in situ by treatment of the solution with aqueous alkali metal carbonate, bicarbonate, or hydroxide at room temperature. The organic layer containing the phosphoranyl intermediate is separated, washed with water, and dried in the usual fashion. The carbonyl reactant shown in the reaction scheme is then added to the dry solution of the phosphoranyl intermediate and the final step of the reaction then takes place at room temperature again within a relatively brief reaction time of from about 2 to 20 hours. The desired product represented by the formula $QCH=CHR^3$ is recovered by techniques known to those skilled in organic chemical laboratory procedures such as chromatography on a silica gel column.

The halide reactants of the formula $QCH_2X$ of Scheme 1 are produced from the corresponding 7-amino or 7-acylamino-3-hydroxymethyl-ceph-3-em-4-carboxylic acid derivatives by methods which are known in principle.

Conversion of the halide reactant of the formula $R^3CH_2X$ according to Scheme 2 to the phosphoranyl intermediate may be carried out with either the chloride, bromide or iodide (X=Cl, Br, or I). If desired the chloride or bromide may be transformed to the iodide as before, but this is not essential. Reaction with the triarylphosphine such as triphenylphosphine is carried out either without a solvent or in an organic liquid vehicle which is inert under the reaction conditions. Room temperature or elevated temperatures for a period of from 1 to 24 hours at 20° C. to 150° C. may be employed. The triarylphosphonium salt ordinarily precipitates and is collected on a filter. It is then dissolved in a suitable liquid organic solvent such as dimethylsulfoxide or one which is immiscible with water such as ether, or tetrahydrofuran, and treated with a base such as butyl lithium, phenyl lithium, sodium methoxide, or sodium hydride for a period of from several minutes to several hours at a temperature in the range of −40° C. to +50° C. The carbonyl reactant is then added to the dry reaction solution and the reaction is allowed to take place at −40° C. to +50° C. for from one to several hours. The desired product represented by the formula

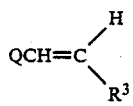

is recovered as before.

Scheme 1 has been found convenient for preparation of those substances of the formula QCH=CHR³ in which R³ is lower alkyl, phenylalkyl, naphthalkyl, haloalkyl, or alkoxyalkyl in the cis-(Z) configuration. According to one variation of Scheme 1, which we refer to as Method A, 7β-[α(N-t-butoxy-carbonylamino)-α-(p-hydroxyphenyl)acetamido]-3-chloromethyl-3-cephem-4-carboxylic acid benzhydryl ester is used as halide reactant. This is illustrated in Procedures 4, 5, and 6 hereof.

A further variation of Scheme 1 which we have found convenient is similar to Method A in that 7β-[α-(N-t-butoxycarbonylamino)-α-(p-hydroxyphenyl)acetamido]-3-chloromethyl-3-cephem-4-carboxylic acid benzhydryl ester is employed as starting material, but in Method B chloroacetaldehyde is employed to produce the blocked 7-aminocephalosporanic acid having the 3-chloro-1-propen-1-yl group in the 3-position. The latter material possesses antibacterial activity, but not to an outstanding extent. In Method B the 3-chloro-1-propen-1-yl compound is employed as an intermediate and converted first to the corresponding 3-iodo-1-propen-1-yl compound which is then converted with heteroaromatic thiols to produce 3-heteroarylthioprop-1-en-1-yl-cephalosporin derivatives.

A further variation of Scheme 1 we refer to as Method C. In this variation 7-amino-3-chloromethyl-3-cephem-4-carboxylic acid benzhydryl ester is prepared as before and the 7-amino group is protected by reaction with benzaldehyde to produce the benzylidene protecting group.

The latter is then treated with triphenylphosphine to provide the phosphonium salt which is then converted with base to the phosphoranyl intermediate and the latter is treated with an aldehyde to give the 3-substituted vinyl-7-aminocephalosporanic acid which then may be acylated to introduce the desired acyl group into the 7-position.

Two variations of Scheme 2 are proposed. In the first, Method D, 3-hydroxymethyl-7-phenylacetamido-3-cephem-4-carboxylic acid prepared as described above in which the carboxylic acid is protected as the benzhydryl ester is converted to the corresponding 3-formyl compound. The latter is then allowed to react with the phosphoranyl intermediate derived from a halide of the formula R³CH₂X as shown in Scheme 2, and the desired 7-acylamino group is introduced by acyl exchange.

Method E is a further variation of Reaction Scheme 2 in which blocked 7-p-hydroxyphenylglycylamido-3-formyl-3-cephem-4-carboxylic acid is used as carbonyl reactant.

7-Phenylacetamidocephalosporanic acid is a convenient starting material in view of its ready availability. The acetoxy group thereof may be readily hydrolyzed enzymatically employing wheat bran as the enzyme source to yield 7-phenylacetamido-3-hydroxymethyl-ceph-3-em-4-carboxylic acid. The carboxylic acid group may be protected by conversion to the benzhydryl ester by treatment of the acid with diphenyldiazomethane. The ester is then treated with phosphorus pentachloride under known conditions which result in cleavage of the 7-phenylacetyl group and conversion of the 3-hydroxymethyl group to a 3-chloromethyl group. The production of 7-amino-3-chloromethyl-3-cephem-4-carboxylic acid benzhydryl ester by these methods is illustrated in Procedures 1 and 2.

Alternatively the 7-phenylacetamido-3-hydroxymethylceph-3-em-4-carboxylic acid may be converted to the 3-halomethyl compound and thence to the phosphoranyl intermediate followed by reaction with an aldehyde to produce the substituted 3-vinylcephalosporin according to one of the variants of Reaction Scheme 1.

The cephalosporin-3-carboxaldehyde represented by the formula QCH=O in the above reaction scheme which serves as carbonyl reactant in Reaction Scheme 2 is produced by oxidation of a 7-acylamino-3-hydroxymethyl-ceph-3-em-4-carboxylic acid ester as is described in U.S. Pat. No. 3,351,596 cited above. Reaction Scheme 2 is the less preferred of the two routes shown, and does not seem to be suitable for the propenyl products of Formula XIII.

The compounds having the formula QCH=CHR³ exist in the cis(Z)- and trans(E)-configurations. Those compounds which have the cis(or Z)-configuration are preferred. They have greater antibacterial activity than the corresponding substances having the trans(or E)-configuration. The compounds of Formula XIV are useful as intermediates for the preparation of other cephalosporins having the formula QCH=CHR³ wherein R³ is the methylene group substituted with the residue of a nucleophilic group such as the mercapto, alkylmercapto, arylmercapto, or heteroarylmercapto groups such as 1,2,3-triazol-5-ylmercapto and 2-methyl-6-pyridinylmercapto. This is illustrated below in Procedure 20. The iodomethyl compounds are preferred as intermediates for nucleophilic displacement processess.

Scheme 1 is adapted to preparation of a product of Formula XIV by substitution of the appropriate carbonyl reactant of the formula XAlkCHO for the R³CHO reactant shown.

PREPARATIVE PROCEDURES

Procedure 1

Benzhydryl 3-Hydroxymethyl-7β-phenylacetamido-3-cephem-4-carboxylate (Compound 1)

To a stirred suspension of phosphate buffer (pH 7, 162.5 ml) and wheat bran (20 g, dry) at room temperature was added 7-phenylacetamidocephalosporanic acid sodium salt (5 gm, 12.1 mmole) in one portion. The progress of the reaction was monitored by HPLC until the hydrolysis was complete (5 hours). The suspension was filtered to remove the wheat bran and the filtrate was cooled to 5°–10° C. for extractive esterification. To the cooled solution was added methylene chloride (32 ml) followed by a 0.5M solution of diphenyldiazomethane in methylene chloride (24 ml). The pH was then adjusted to 3.0 with 28% phosphoric acid. After 1 hour the reaction mixture was allowed to rise to 20° C. Heptane (56 ml) was slowly added and the resulting crystalline title product was recovered by filtration. Yield of product was 3.0 gm (50%).

Procedure 2

Benzhydryl 7β-Amino-3-chloromethyl-3-cephem-4-carboxylate (2)

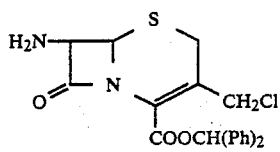

To a slurry of PCl$_5$ (8.3 g, 40 mmoles) in CH$_2$Cl$_2$ (1000 ml) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate (1), 5.1 g, 10 mmoles, with stirring at −40° C., in one portion. The mixture was stirred at −10° C. for 15 minutes and allowed to stand at −10° C. to −15° C. for 7 hours. To the cooled solution (1°–20° C.) was added propane-1,3-diol (10 ml) and the mixture was allowed to stand at −20° C. for 16 hours and then at room temperature for 20 minutes with stirring. The resulting solution was washed with ice-water (2×20 ml) and saturated aqueous NaCl (10 ml), dried over MgSO$_4$ and concentrated in vacuo. The gummy residue (12 g) was dissolved in a mixture of CHCl$_3$ and n-hexane (2:1), and subjected to chromatography using a silica gel column (200 g) and the same solvent as eluant. Fractions containing the title compound were evaporated in vacuo and the residue triturated with n-hexane to give (2) (2.1 g, 51%), melting at 110° C. (dec.).

IR: $\nu_{KBr}$ 3400, 2800, 1785, 1725 cm$^{-1}$.

UV: $\lambda_{max}^{EtOH}$ 265 nm (E$_{1\ cm}^{1\%}$ 160).

NMR: $\delta_{ppm}^{DMSO-d6}$+CDCl$_3$ 3.69 (2H, s) 4.43 (2H, s), 5.09 (1H, d, J=4.5 Hz), 5.24 (1H, d, J=4.5 Hz), 6.87 (1H, s), 7.3 (10H, m).

Procedure 3

Benzhydryl 7β-[D-2-(t-butoxycarbonylamino)-2-(p-hydroxyphenyl)-acetamido]-3-chloromethyl-3-cephem-4-carboxylate (Compound 3)

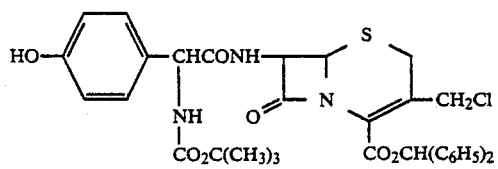

To a mixture of 20.7 g (0.05 mol) of benzyhydryl 7-amino-3-chloromethyl-3-cephem-4-carboxylate (2) and 20 g (0.075 mol) of D-2-(t-butoxycarbonylamino)-2-(p-hydroxyphenyl)-acetic acid in 500 ml of dry tetrahydrofuran (THF) was added 15.45 g (0.075 mol) of N,N'-dicyclohexylcarbodiimide (DCC) and the mixture was stirred at room temperature for 2 hours and evaporated to dryness. The residue was dissolved in 1 l. of ethyl acetate (AcOEt) and the insoluble dicylohexylurea was removed by filtration. The filtrate was washed with an aqueous sodium bicarbonate solution, water and saturated aqueous NaCl solution, dried on anhydrous sodium sulfate and evaporated to dryness. The oily residue was chromatographed on a column of silica gel (Wako gel C-100, 500 g) by eluting with 4 liters of chloroform and 6 liters of 1% chloroform-methanol. The desired fractions were combined and evaporated to dryness. The oily residue was triturated with ether-isopropyl ether to give 30.6 g (92%) of 3.

IR: $\nu_{max}^{KBr}$ cm$^{-1}$ 1790, 1710, 1670, 1500, 1360, 1230, 1150.

NMR: $\delta^{CDCl_3}$ ppm 1.45 (9H, s, C—CH$_3$), 3.4 (2H, br-s, 2—H), 4.28 (2H, s, CH$_2$Cl), 4.86 (1H, d, 4.5 Hz, 6—H), 5.12 (1H, d, 6 Hz, CH—CO), 5.68 (1H, d-d, 8 & 4.5 Hz, 7—H), 6.63 (2H, d, 9 Hz, phenyl—H), 6.93 (1H, s, CH—Ph$_2$), 7.08 (2H, d, 9 Hz, phenyl—H), 7.0–7.5 (10H, m, phenyl—H).

The oily residue may be used without chromatographic purification in Procedure 4.

Procedure 4

Benzhydryl 7β-[D-2-(t-butoxycarbonylamino)-2-(p-hydroxyphenyl)-acetamido]-3-iodomethyl-3-cephem-4-carboxylate (Compound 4)

A mixture of 26.6 g (0.04 mol) of 3 and 18 g (0.12 mol) of sodium iodide in 400 ml of acetone was stirred at room temperature for 2 hours and evaporated to dryness. The residue was extracted with 400 ml of ethyl acetate and the extract was washed with an aqueous Na$_2$S$_2$O$_3$ solution, water, and a saturated aqueous NaCl solution. After evaporation of the solvent, the residue was triturated with ether-isopropyl ether to give 27 g (89%) of the title compound. The ethyl acetate solution may be used directly in the next step (Compound 5) without isolation of Compound 4 if desired.

IR: $\nu_{max}^{KBr}$ cm$^{-1}$ 1790, 1710, 1670, 1500, 1360, 1220, 1150.

NMR: $\delta^{CDCl_3}$ ppm 1.47 (9H, s, C—CH$_3$), 3.3–3.6 (2H, m, 2—H), 4.20 (2H, s, CH$_2$), 4.89 (1H, d, 4.5 Hz, 6—H), 5.12 (1H, d, 6 Hz, CH—CO), 5.68 (1H, d-d, 8 & 4.5 Hz, 7—H), 6.62 (2H, d, 9 Hz, phenyl—H), 6.92 (1H, s, CHPh$_2$), 7.08 (2H, d, 9 Hz, phenyl—H), 7–7.5 (10H, m, phenyl—H).

Procedure 5

Benzhydryl 7β-[D-2-(t-butoxycarbonylamino)-2-(p-hydroxyphenyl)-acetamido]-3-(triphenylphosphonio)methyl-3-cephem-4-carboxylate iodide (Compound 5)

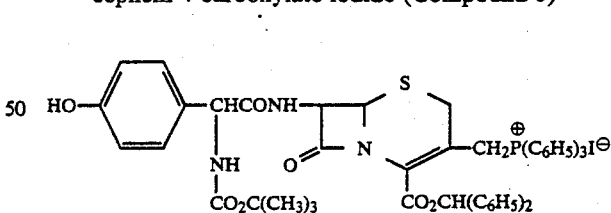

A mixture of 15.1 g. (0.02 mol.) of 4 and 15.7 g. (0.06 mol.) of triphenylphosphine in 200 ml. of ethyl acetate was stirred at room temperature for one hour. The resulting precipitate was collected by filtration to give 17.4 g. (85.5%) of 5, melting at 170°–180° C. The filtrate was concentrated to 100 ml. and the concentrate was diluted with 500 ml. of ether to give the second crop 1.1 g.) of 5. The total yield was 18.5 g. (91%). The overall yield of 5 from 2 is 74.5%. This can be increased to 87.5% by omission of the purification and isolation steps as indicated above.

IR: $\nu_{max}^{KBr}$ cm$^{-1}$ 1780, 1670, 1490, 1420, 1350, 1240, 1150, 1090.

NMR: $\delta^{DMSO}$ ppm 1.42 (9H, s, C—CH$_3$), 3.45 (2H, br-s, 2—H), 5-5.4 (3H, m, 3—H & 6—H), 5.7 (1H, m, 7—H), 6.63 (2H, d, 9 Hz, phenyl—H), 7.1-7.45 (12H, m, phenyl—H), 7.5-7.9 (15H, m, phenyl—H).

Anal. Calcd for C$_{52}$H$_{49}$N$_3$O$_7$SPI: C, 61.36; H, 4.85; N, 4.13; S, 3.15. Found: C, 61.26; H, 4.82; N, 4.11; S, 3.92.

Procedure 6

Benzhydryl 7β-[D-2-(t-butoxycarbonylamino)-2-(p-hydroxyphenyl)-acetamido]-3-[(Z)-1-propen-1-yl]ceph-3-em-4-carboxylate (Compound 6)

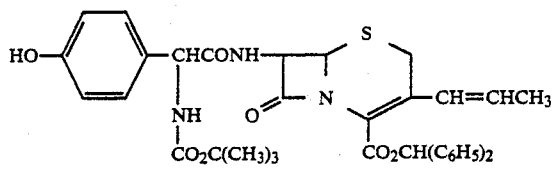

To a solution of 1.8 g. (1.77 m mol) of 5 in 100 ml. of chloroform was added 100 ml. of water containing 2 ml. (2 m mol) of N sodium hydroxide and the mixture was shaken for 5 minutes. The organic layer was separated, washed with water and dried on anhydrous sodium sulfate. The chloroform solution being filtered, the filtrate was concentrated to 50 ml. under reduced pressure. To the concentrate was added 1 g. of acetaldehyde and the mixture was stirred at room temperature for 2 hours and evaporated to dryness. The oily residue was chromatographed on a silica gel column (Wako-gel C-200, 50 g.) by eluting with chloroform and chloroform-methanol (99:1). The desired fractions were collected and evaporated to give 318 mg. (28%) of the product 6, m.p. 120°-130° C. (dec.).

IR: $\nu_{max}^{KBr}$ cm$^{-1}$ 1780, 1670, 1710, 1490, 1360, 1210, 1150.

NMR: $\delta^{CDCl_3}$ ppm 1.3-1.5 (12H, m, C—CH$_3$), 3.22 (2H, br-s, 2H), 4.90 (1H, d, 4.5 Hz, 6—H), 5.15 (1H, br-d, CH—CO), 5.5-6.1 (3H, m, CH=CH & 7—H), 6.63 (2H, d, 9 Hz, phenyl—H), 6.91 (1H, s, CH—Ph), 7.09 (2H, d, 9 Hz, phenyl—H), 7.2-7.5 (10H, m, phenyl—H).

Procedure 7

Sodium 7β-[D-2-amino-2-(p-hydroxyphenyl)acetamido]-3-[(Z)-1-propen-1-yl]-3-ceph-em-4-carboxylate (Compound 7, BMY-28100 Sodium Salt)

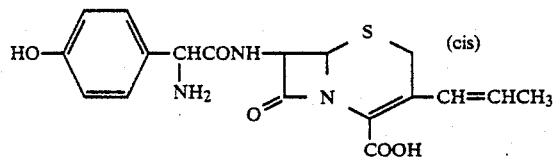

A mixture of 318 mg. (0.48 m mol) of 6 and 2.5 ml. of trifluoroacetic acid (TFA) was stirred at room temperature for one hour and then diluted with 50 ml. of ether and 50 ml. of isopropyl ether. The precipitate separated was collected by filtration and washed with ether to give 188 mg. (77%) of the trifluoroacetate of 7, which was dissolved in 2 ml. of methanol (MeOH). To the solution was added 2 ml. (2 m mol) of a solution of sodium 2-ethylhexanoate (SEH) in ethyl acetate and the mixture was diluted with 30 ml. of ethyl acetate to separate the precipitate, which was collected by filtration, washed with ether and dried in vacuo over P$_2$O$_5$ to give 144 mg. (73% from 6) of crude 7. The crude product (135 mg.) was dissolved in 10 ml. of water and the solution was chromatographed on a column (25 mm × 100 mm) using about 20 ml. of the packing in the PrepPak-500/C$_{18}$ (Waters). The column was eluted with water and the eluate containing the desired product were concentrated to 5 ml. and lyophilized to give 93 mg. (69%) of 7. M.p. 200° C. (grad. dec.). Estimated purity 60% (by HPLC).

IR: $\nu_{max}^{KBr}$ cm$^{-1}$ 1760, 1660, 1590, 1400, 1360, 1250.

UV: $\nu_{max}^{Phosphate\ buffer\ pH\ 7}$ nm($\epsilon$) 227 (11300), 280 (8200).

NMR: $\delta^{D_2O}$ ppm 1.65 (3H, d, 6 Hz, —C—CH$_3$), 3.21 (1H, d, 18 Hz, 2—H), 3.52 (1H, d, 18 Hz, 2—H), 5.12 (1H, d, 4.5 Hz, 6—H), 5.68 (1H, d, 4.5 Hz, 7—H), 5.5-5.9 (1H, m, vinyl—H), 5.95 (1H, d, 11.5 Hz, vinyl—H), 6.94 (2H, d, 8 Hz, phenyl—H), 7.36 (2H, d, 8 Hz, phenyl—H).

Procedure 8

7β-[D-2-Amino-2-(p-hydroxyphenyl)acetamido]-3-[(E)-1-propen-1-yl]-3-cephem-4-carboxylic Acid (Compound 8, BB-S1067)

The crude product produced in Procedure 7, crude 7 prior to chromatographic purification, 11.9 g., was dissolved in 50 ml. of 0.01M phosphate buffer (pH 7.2)-methanol (85:15) and the solution was adjusted to pH 6 with 6N hydrochloric acid. The solution was subjected to preparative high performance liquid chromatography (HPLC) (prepPAK-500/C$_{18}$, System 500, Waters) by eluting with 0.01M phosphate buffer (pH 7.2) containing 15% methanol. The eluate was monitored by analytical HPLC and the first 4 l. fraction was found to contain cis isomer (BMY-28100). The second 1 l. fraction containing the trans isomer was collected and concentrated to 500 ml. The concentrate was adjusted to pH 3 with dilute hydrochloric acid and chromatographed on an HP-20 column (100 ml.) by eluting with 1 l. each of water and 30% methanol. The latter eluate, volume about 300 ml., was concentrated to 10 ml. and lyophilized to give 290 mg. of the crude trans isomer (55% pure). This material was dissolved in 100 ml. of 50% methanol and treated with activated carbon. The filtrate was concentrated to a volume of 20 ml. and allowed to stand overnight at 5° C. The product crystallized as colorless prisms which were collected by filtration and dried in vacuo, 129 mg., m.p. 230° C. (dec.).

IR: $\nu_{max}^{KBr}$ cm$^{-1}$ 1760, 1680, 1590, 1550, 1520, 1450, 1390, 1350, 1240.

UV: $\lambda_{max}^{phosphate\ buffer\ (pH\ 7)}$ nm($\epsilon$) 228 (13000), 292 (16900).

NNR: $\delta^{D_2O+Na_2CO_3}$ ppm 1.89 (3H, d, 6 Hz, C=C—CH$_3$), 3.60 (2H, s, 2—H), 5.13 (1H, d, 4.5 Hz, 6—H), 5.20 (1H, s, CH—CO), 5.68 (1H, d, 4.5 Hz, 7—H), 5.99 (1H, d-q, 16 & 6 Hz), 6.54 (1H, d, 16 Hz), 6.98 (2H, d, 9 Hz, phenyl—H), 7.41 (2H, d, 9 Hz, phenyl—H).

Procedure 9

Crystalline 7β-[D-2-amino-(p-hydroxyphenyl)acetamido]-3-[(Z)-1-propen-1-yl]-3-cepehm-4-carboxylic Acid (Compound 9, BMY-28100)

The first 4 l. fraction obtained in the preparative HPLC in Procedure 8 containing the cis isomer (BMY-28100) was concentrated to a volume of 2 l. and the concentrate adjusted to pH 3 with dilute hydrochloric acid. The solution was charged to a column containing HP-20 (1 l.) and the column was washed with 6 l. of water until the pH of the effluent was pH 7. The column was then eluted with 4 l. of 30% aqueous methanol. The eluate solution was monitored by HPLC and the appropriate fractions were combined (about 2.5 l.) and concentrated to 50 ml. at a temperature less than 40° C. at reduced pressure. A crystalline precipitate formed. The concentrate was cooled at 0° C. for two hours and the crystalline precipitate collected by filtration, washed with 80% aqueous acetone, then with 100% acetone and then dried in vacuo over $P_2O_5$ yielding 4.09 g. of the pure crystalline desired product, melting point 218°–220° C. (dec.), colorless prisms 95% pure as determined by HPLC assay.

IR: $\nu_{max}^{KBr}$ cm$^{-1}$ 1750, 1680, 1560, 1520, 1460, 1390, 1350, 1270, 1235.

UV: $\lambda_{max}^{phosphate\ buffer\ (pH\ 7)}$ nm($\epsilon$) 228 (12300), 279 (9800).

NMR: $\delta^{D_2O+NaHCO_3}$ ppm 1.71 (3H, d, 6 Hz, C—CH$_3$), 3.27 (1H, d, 18 Hz, 2—H), 3.59 (1H, d, 18 Hz, 2—H), 5.18 (1H, d, 4.5 Hz, 6—H), 5.22 (1H, s, CHCO), 5.73 (1H, d, 4.5 Hz, 7—H), 5.5–6.0 (1H, m, CH=C), 6.02 (1H, d, 11 Hz, CH=C), 6.98 (2H, d, 9 Hz, pheny-1—H), 7.41 (2H, d, 9 Hz, phenyl—H).

Anal. Calcd for $C_{18}H_{19}N_3O_5S \cdot \frac{1}{2}H_2O$: C, 54.26; H, 5.06; N, 10.55; S, 8.05 Found: C, 54.15, 54.19; H, 5.13, 5.08; N, 10.30, 10.42; S, 8.38, 8.04.

The mother liquor from the foregoing crystallization was concentrated to a volume of 10 ml. and treated with 20 ml. of acetone. After keeping the solution overnight in the refrigerator a crystalline precipitate had formed which was collected by filtration and dried in vacuo over $P_2O_5$, weight 670 mg. (90% pure by HPLC). A portion of this material, 560 mg., was dissolved in 200 ml. of 50% aqueous methanol and the solution was treated with 0.5 g. of activated carbon and filtered. The filtrate was concentrated at reduced pressure and 40° C. to a volume of 20 ml. and then kept for five hours at 5° C. The product crystallized and was collected by filtration, washed with acetone, and dried in vacuo over $P_2O_5$ to yield 227 mg. of crystalline BMY-28100 (98% pure by HPLC). Lyophilization of the mother liquor yielded 181 mg. of BMY-28100 which was 95% pure (HPLC).

Procedure 10

Dephenylmethyl 7β-[D-2-(t-butoxycarbonylamino)-2-(p-hydroxyphenyl)acetamido]-3-vinyl-3-cephem-4-carboxylate (Compound 10)

A solution of 3 g. (2.95 m. mol.) of benzhydryl 7-[2-(N-t-butoxycarbonylamino)-2-(p-hydroxyphenyl)acetamido]-3-(triphenylphosphonio)methyl-3-cephem-4-carboxylate iodide (5) in 50 ml of chloroform was shaken with a mixture of 3 ml. (3 m. mol.) of 1N NaOH and 50 ml. of water at room temperature for 1 minute. The organic layer was separated after the addition of a saturated NaCl solution (20 ml) and washed with water (3×30 ml.). To the organic solution was added 2.5 ml. of 35% aqueous formaldehyde with vigorous stirring under water-cooling. The stirring was continued for 20 minutes. The organic layer was separated, dried over anhydrous $Na_2SO_4$ and concentrated in vacuo. The concentrate was placed on a column of silica gel, which was eluted with CHCl$_3$ (600 ml.) and 2% MeOH in CHCl$_3$ (800 ml.) to give 850 mg. (45%) of the title compound. TLC: Rf 0.48 [silica gel, MeOH—CHCl$_3$ (1:10)].

Procedure 11

7β-[D-2-Amino-2-(p-hydroxyphenyl)acetamido]-3-vinyl]-3-cephem-4-carboxylic Acid (Compound 11, BB-S-1064)

A mixture of 850 mg. (1.32 m. mol.) of 10, and 5 ml. of 90% aqueous trifluoroacetic acid (TFA) was allowed to stand at room temperature for one hour and concentrated to ca. 1 ml. in vacuo. The concentrate was triturated with 20 ml. of diisopropyl ether to give 679 mg. of yellow powder, which was dissolved in 3 ml. of methanol and subsequently diluted with 30 ml. of water. The solution was passed through a column of HP-20 (50 ml.), which was washed with 200 ml. of water and eluted with 250 ml. of 30% methanol. The eluate containing the desired compound was concentrated and lyophilized to give 197 mg. (31%) of the title compound, estimated purity, 60% by HPLC, m.p. 190° C. (dec.).

IR: $\nu_{max}^{KBr}$ cm$^{-1}$ 1760, 1680, 1615–1570, 1520.

UV: $\lambda_{max}^{phosphate\ buffer\ (pH\ 7)}$ nm($\epsilon$) 228 (13500), 283 (14400).

NMR: $\delta^{D_2O}$ ppm 3.6 (2H, s, SCH$_2$), 5.51 (1H, d, 5 Hz, 6—H), 5.73 (1H, d, 5 Hz, 7—H), 7.03 (2H, d, 8 Hz, phenyl—H), 7.45 (2H, d, 9 Hz, phenyl—H).

Procedure 12

Diphenylmethyl 7β-[D-2-(t-butoxycarbonylamino)-2-(p-hydroxyphenyl)-acetamido]-3-[(Z)-1-buten-1-yl]-3-cephem-4-carboxylate (Compound 12)

A solution of 3 g. (2.95 m. mol.) of 5 in 50 ml. of CHCl$_3$ was mixed with a mixture of 3.2 ml. (3.2 m. mol.) of 1N NaOH and 50 ml. of water and the mixture was shaken at room temperature for 3 minutes. The organic layer was separated, washed with water (3×30 ml.) and a saturated NaCl solution, and dried over anhydrous $Na_2SO_4$. To the solution was added 1.71 g. (29.5 m. mol.) of propionaldehyde. The mixture was stirred overnight at room temperature and concentrated under reduced pressure. The concentrate was charged on a column of silica gel, which was eluted with 1–2% methanol in CHCl$_3$. The fractions showing a spot of Rf 0.30 (TLC, MeOH—CHCl$_3$=1:10) were combined and evaporated to give 1.08 g. (55%) of the title compound.

IR: $\nu_{max}^{KBr}$ cm$^{-1}$ 1780, 1680, 1500.

Procedure 13

Sodium 7β-[D-2-amino-2-(p-hydroxyphenyl)acetamido]-3-[(Z)-1-buten-1-yl]-3-cephem-4-carboxylate (Compound 13, BB-S1058 Sodium Salt)

A solution of 1.08 g. (1.61 m. mol.) of 12 in 11 ml. of TFA containing 1% of water was allowed to stand for one hour at room temperature. The mixture was concentrated to about 2 ml. in vacuo and the resulting syrup was triturated with about 20 ml. of diisopropyl ether to give 796 mg. of yellow powder. The powder was dissolved in 3 ml. of methanol and the solution was treated with 3 ml. of 0.8M SEH in ethyl acetate (AcOEt) to afford a precipitate, which was filtered, washed with diisopropyl ether and dissolved in 5 ml. of water. The solution was passed through a column, packed with the packing (80 ml.) of a prepPAK-500/$C_{18}$ cartrige (Waters), which was washed with water and eluted successively with 10% methanol, 20% methanol and 30% methanol. The desired fractions (monitored by HPLC) were combined, concentrated and lyophilized to give 118 mg. (9.4%) of the title compound, estimated purity 55% (by HPLC), darkened when heated in a glass capillary tube >180° C.

IR: $\nu_{max}^{KBr}$ cm$^{-1}$ 1755, 1660, 1580.

UV: $\lambda_{max}^{phosphate\ buffer\ (pH\ 7)}$ nm($\epsilon$) 228(10900), 278(7200).

NMR: $\delta^{D2O}$ ppm 0.81 (3H, t, 7.5 Hz), 1.7–2.2 (2H, m), 3.25 (2H, ABq), 5.01 (1H, d, 5 Hz), 5.50 (1H, d-t, 7.5 & 12 Hz), 5.58 (1H, d, 5 Hz), 5.78 (1H, d, 12 Hz), 6.86 (2H, d, 8 Hz), 7.26 (2H, d, 8 Hz).

Procedure 14

Diphenylmethyl 7β-[D-2-(t-butoxycarbonylamino)-2-(p-hydroxyphenyl)acetamido]-3-[(Z)-3-phenyl-1-propen-1-yl]-3-cephem-4-carboxylate (Compound 14)

A solution of 3 g. (2.95 m. mol.) of 5 in 50 ml of CHCl$_3$ was shaken with a mixture of 3.2 ml. (3.2 m. mol.) of 1N NaOH and 50 ml. of water for one minute. The organic layer was separated after the addition of a saturated NaCl solution (20 ml.), washed with water (3×30 ml.) and a saturated NaCl solution and dried with anhydrous Na$_2$SO$_4$. To the solution was added 7.2 g. (30 m. mol.) of 50% phenylacetaldehyde and the mixture was stirred overnight at room temperature. The reaction mixture was concentrated in vacuo and the concentrate was purified on a column of silica gel (75 g.) using 1% MeOH/CHCl$_3$ to give 800 mg. (37%) of the title compound. Thin layer chromatography (TLC): Rf 0.33 (silica gel, MeOH—CHCl$_3$1:10). IR (KBr): 1780, 1710–1680 cm$^{-1}$. This compound was used for Procedure 15 without further purification.

Procedure 15

7β-[D-2-Amino-2-(p-hydroxyphenyl)acetamido]-3-[(Z)-3-phenyl-1-propen-1-yl]-3-cephem-4-carboxylic acid (Compound 15, BB-S1076)

A solution of 800 mg. (1.09 m. mol.) of 14 in 4 ml. of 90% TFA was allowed to stand for two hours. The reaction mixture was concentrated and the concentrate was triturated with diisopropyl ether to give 490 mg. of yellow powder. A solution of the powder in 2 ml. of methanol was mixed with 20 ml. of water and charged on a column of HP-20 (50 ml.), which was washed with water (250 ml.) and eluted with 30% methanol (250 ml.) and 75% methanol (300 ml.) successively. The 75% methanol eluate was concentrated and lyophilized to give 302 mg. of the crude product, which was dissolved in 10 ml. of 75% methanol and chromatographed on a column using the packing (80 ml.) of a PrepPAK-500/$C_{18}$ cartridge (Waters). The column was eluted with 75% methanol to afford 158 mg. (31%) of the desired product. Estimated purity, 65% (by HPLC). It darkened when heated in a capillary tube over 175° C.

IR: $\nu_{max}^{KBr}$ cm$^{-1}$ 1760, 1680, 1600–1580, 1520.

UV: $\nu_{max}^{phosphate\ buffer\ (pH\ 7)}$ nm($\epsilon$) 280 (8900).

NMR: $\delta^{DMSO-D6/D2O}$ (5/1) ppm 4.45 (2H, d, 4 Hz, CH$_2$Ph), 4.87 (1H, s, CHND$_2$), 6.7 (2H, d, 9 Hz, Ph), 6.9–7.5 (7H, m Ph).

Procedure 16

Diphenylmethyl 7β-[D-2-(t-butoxycarbonylamino)-2-(p-hydroxyphenyl)-acetamido]-3-[(Z)-3-methoxy-1-propen-1yl]-3-cephem-4-carboxylate (Compound 16)

A solution of 3.0 g. (2.95 m. mol.) of 5 in CHCl$_3$ (100 ml.) was treated with a mixture of 2N NaOH (1.8 ml.) and water (100 ml.) at room temperature for 5 minutes. The organic phase was separated, washed with water (50 ml.) and aqueous NaCl (50 ml.) dried and evaporated to ca. 10 ml. The resulting red ylide solution was treated with methoxyacetaldehyde (1.3 ml., 15 m. mol.) at room temperature for 15 minutes. After evaporation of the solvent, the residue was chromatographed on a column of silica gel (100 g.), eluting with toluene-AcOEt (3:1 and 1:1) to afford the title compound (750 mg., 38%).

NMR: $\delta^{CDCl3+D2O}$ ppm 1.45 (9H, s, t-Bu), 3.15 (3H, s, OCH$_3$), 3.27 (2H, s, 2—CH$_2$), ca. 3.5 (2H, m, —CH$_2$—OMe), 4.90 (1H, d, 5.0 Hz, 6—H), 5.12 (1H, s, —CH—ND—), ca. 5.5 (1H, m, =CH—CH$_2$—), 5.72 (1H, d, 7—H), 6.18 (1H, d, 12 Hz, —CH=CH—CH$_2$—), 6.65 & 7.10 (each 2H, each d, HO—Ph—), 6.90 (1H, s, —CHPh$_2$), 7.3(10H, s, Ph).

Procedure 17

7β-[D-2-Amino-2-(p-hydroxyphenyl)acetamido]-3-[(Z)-3-methoxy-1-propen-1-yl]-3-cephem-4-carboxylic Acid (Compound 17, BB-S1092)

Compound 16 was deblocked with TFA (3 ml.) at room temperature for one hour. Evaporation of the solvent followed by precipitation from isopropyl ether gave the trifluoroacetate of the product, which was purified by HP-20 column chromatography. The column was washed with H$_2$O (500 ml.) and eluted with 30% MeOH (500 ml.) to afford 350 mg. (75%) of desired product. Estimated purity, 90% (by HPLC). M.p. 160° C. (dec.).

IR: $\nu_{max}^{KBr}$ cm$^{-1}$ 3400, 3180, 1760, 1680.

UV: $\lambda_{max}^{phosphate\ buffer\ pH\ 7}$ nm($\epsilon$) 228(11500), 279 (9400).

NMR: $\delta^{D2O}$ ppm 3.40 (3H, s, OCH$_3$), 3.40 (2H, ABq, 2—CH$_2$), 4.0 (2H, m, —CH$_2$OMe), 5.19 (1H, d, 4.5 Hz, 6—H), 5.25 (1H, s, —CH—ND$_2$), 5.77 (1H, d, 7—H). ca. 5.8 (1H, m, =CH—CH$_2$—), 6.20 (1H, d, 11 Hz, —CH=CH—CH$_2$), 7.05 & 7.45 (each 2H, each d, HO—Ph—).

Procedure 18

Diphenylmethyl 7β-[D-2-(t-butoxycarbonylamino)-2-(p-hydroxyphenyl)-acetamido]-3-[(Z)-3-chloro-1-propen-1-yl]-3-cephem-4-carboxylate (Compound 18)

A solution of 5 (5.0 g., 4.9 m. mol.) in CHCl$_3$ (100 ml.) was treated with a mixture of 2NNaOH (2.9 ml., 5.8 m. mol.) and water (100 ml.) at room temperature for 5 minutes. The organic phase was separated and washed with water (50 ml.) and a saturated NaCl solution (50 ml.), and dried over anhydrous Na$_2$SO$_4$. The filtrate was evaporated to ca. 20 ml. and chloroacetaldehyde (2.0 ml., 25 m. mol.) was added. The mixture was stirred at room temperature for 30 minutes and evaporated in vacuo. The residual syrup was chromatographed on a column of silica gel (100 g.), eluting with toluene-AcOEt (3/1) to afford the title compound 18 (900 mg., 27%).

NMR: $\delta^{CDCl_3+D_2O}$ ppm 1.45 (9H, s, t-Bu), ca. 3.3 (2H, m, 2—CH$_2$), 3.5–4.0 (2H, m, —CH$_2$—Cl), 4.92 (1H, d, 5.0 Hz, 6—H), 5.12 (1H, s, —CH—ND—), ca. 5.7 (2H, m, 7—H & =CH—CH$_2$), 6.15 (1H, d, 11 Hz, 3—CH=CH—CH$_2$—), 6.63 & 7.10 (each 2H, each d, HO—Ph—), 6.89 (1H, s, CHPh$_2$), 7.3 (10H, s, Ph).

Deblocking of this substance with TFA as described in the preceding examples (e.g. Proc. 7, 11 etc.) yielded 7-[D-2-amino-2-(p-hydroxyphenyl)acetamido]-3-[(Z)-3-chloro-1-propen-1-yl]-3-cephem-4-carboxylic acid.

Procedure 19

Diphenylmethyl 7β-[D-2-(t-butoxycarbonylamino)-2-(p-hydroxyphenyl)acetamido]-3-[(E)-3-iodo-1-propen-1-yl]-3-cephem-4-carboxylate (Compound 19)

A mixture of 18 (900 mg., 1.3 m. mol.) and NaI (590 mg., 3.9 m. mol.) in acetone (18 ml) was stirred at room temperature for one hour. After evaporation of the solvent, the residue was dissolved in AcOEt (100 ml.), washed successively with water, aqueous Na$_2$S$_2$O$_3$ and aqueous NaCl, dried and evaporated to give the title compound (1.02 g.).

NMR: $\delta^{CDCl_3+D_2O}$ ppm 1.45 (9H, s, t-Bu), ca. 3.4 (2H, m, 2—CH$_2$), ca. 3.8 (2H, m, —CH$_2$—I), 4.90 (1H, d, 5.0 Hz, 6—H), 5.14 (1H, s, —CH—ND—). 5.73 (1H, d, 7—H), ca. 5.5–6.0 (1H, m, =CH—CH$_2$—), 6.68 & 7.10 (each 2H, each d, HO—Ph—), 6.78 (1H, d, 15 Hz, 3—CH=CH—CH$_2$—), 6.99 (1H, s, CHPh$_2$), 7.35 (10H, s, Ph).

Procedure 20

Diphenylmethyl 7β-[D-2-(t-butoxycarbonylamino)-2-(p-hydroxyphenyl)acetamido]-3-[-3-(1H-1,2,3-triazol-5-yl)thio-1-propen-1-yl]-3-cephem-4-carboxylate (Compound 20)

To a solution of 19 (1.0 g., 1.3 m. mol.) in ethyl acetate (20 ml.) were added propylene oxide (0.27 ml., 3.8 m. mol.) and 0.1M (1H-1,2,3-triazol-4-yl)thiol in ethyl acetate (19 ml.). The mixture was stirred at room temperature for 30 minutes and evaporated under diminished pressure. The residual syrup was chromatographed on a column of silica gel C-200 (50 g.). The desired product was eluted with CHCl$_3$—MeOH (10:1) to afford 800 mg. (83%) of the title compound.

NMR: $\delta^{CDCl_3+H_2O}$ ppm 1.45 (9H, s, t-Bu), ca. 3.3 (4H, m, 2—CH$_2$—& —C H$_2$—S—) 4.80 (1H, d, 5.0 Hz, 6—H), 5.20 (1H, s, —CH—ND—), 5.70 (1H, d, 7—H), ca. 5.95 (1H, m, =CH—CH$_2$—), 6.68 (2H, d, HO—Ph—), 6.90 (1H, s, —CHPh$_2$), 7.25 (10H, s, Ph), 7.52 (1H, s, triazole-4-H).

Procedure 21

7β-[D-2-Amino-2-(p-hydroxyphenyl)acetamido]-3-[-3-(1H-1,2,3,-triazol-5-yl)thio-1-propen-1-yl]-3-cephem-4-carboxylic Acid (Compound 21, BB-S1091)

A mixture of 20 (800 mg.) and TFA (2 ml.) was kept at room temperature for one hour and then evaporated to dryness. To the residue was added isopropyl ether to give yellow precipitate (600 mg.), which was dissolved in water (1 ml.) and charged onto an HP-20 column (100 ml.). The column was washed with water (500 ml.) and eluted with 30 % MeOH and subsequently with 50% MeOH. The fraction containing the desired compound was collected, evaporated and lyophilized to afford 170 mg. (33%) of desired product, estimated purity, 50% (by HPLC), m.p. 180° C. (dec.).

IR: $\nu_{max}^{KBr}$ cm$^{-1}$ 3360, 3280, 1755, 1670.

UV: $\lambda_{max}^{phosphate\ buffer}$ nm($\epsilon$) 235(14100), 252 (12300).

NMR: $\delta^{D_2O+DCl}$ ppm ca. 3.4 (4H, m, 2—CH$_2$—, —CH$_2$—S—), 5.43 (1H, d, 4.5 Hz, 6—H). 5.15 (1H, s, —CH—ND$_2$), ca. 6.0 (2H, m, 7—H and =CH—CH 2—), 6.70 & 7.15 (each 2H, each d, HO—Ph—), 8.05 (1H, s, triazol—4—H).

Procedure 22

Benzhydryl 7β-[D-2-(t-Butoxycarbonylamino)-2-phenylacetamido]-3-(triphenylphosphonio)methyl-3-cephem-4-carboxylate Iodide (Compound 22)

A mixture of 14.5 g. (0.0196 m mol) of benzhydryl 7-[D(—)-α-(t-butoxycarbonylamino)-α-phenylacetamido]-3-iodomethyl-3-cephem-4-carboxylate and 5.24 g. (0.02 mol) of triphenylphosphine in 300 ml of ethyl acetate was stirred at room temperature for 2 hours. To the reaction mixture was added 200 ml of ether to form precipitate, which was collected by filtration and washed with ether to give 14.3 g. (73%) of the title compound. The filtrate was concentrated to 50 ml and the concentrate was diluted with ether to give 2.4 g of the second crop of the product. Total yield 16.7 g. (85%).

IR: $\nu_{max}^{KBr}$ cm$^{-1}$ 1780, 1690, 1480, 1420, 1350, 1240, 1150.

Procedure 23

Benzhydryl 7β-[D-2-(t-Butoxycarbonylamino)-2-phenylacetamido]-3-[(Z)-1-propen-1-yl]-3-cephem-4-carboxylate (Compound 23)

To a solution of 5 g. (5 m mol) of 22 in 200 ml of chloroform was added a mixture of 100 ml of water and 5 ml 5 (m mol) of N sodium hydroxide and the mixture was shaken for 3 minutes. The organic layer separated was washed with water and a saturated NaCl solution, and dried on anhydrous magnesium sulfate. The chloroform solution being filtered, the filtrate was concentrated to 100 ml under reduced pressure. To the concentrate was added 3 ml of acetaldehyde and the mixture was stirred at room temperature for 1.5 hours and evaporated to dryness. The oily residue was chromatographed on a column of silica gel (Kiesel gel 60, 50 g) by eluting with chloroform. The desired fractions were collected and evaporated to dryness and the residue was triturated with n-hexane to give 990 mg (31%) of the title compound (23).

IR: $\nu_{max}^{KBr}$ cm$^{-1}$ 1780, 1710, 1660, 1510, 1490, 1360, 1240, 1210, 1150.

NMR: $\delta^{CDCl_3}$ ppm 1.3–1.5 (12H, m, —C—CH$_3$), 3.22 (2H, s, 2—H), 4.93 (1H, d, 4.5 Hz, 6—H), 5.23 (1H, d, 8 Hz, CH—CO), 5.5–6.2 (3H, m, 7—H & vinyl—H), 6.94 (1H, s, CHPh), 7.2–7.5 (15H, m, phenyl—H).

Procedure 24

Sodium
7β-[D-2-amino-2-phenylacetamido]-3-[(Z)-1-propenyl]-3-cephem-4-carboxylate (Compound 24, BB-S1065)

A mixture of 0.94 g. (1.47 m mol) of 23 and 3 ml of TFA was stirred at room temperature for 30 minutes then diluted with 50 ml of a 1:1 mixture of ether-isopropyl ether to separate ca. 800 mg of precipitate, which was collected by filtration and dissolved in 3 ml of methanol. To the solution was added 4.5 ml (4.5 m mol) of 1M sodium 2-ethylhexanoate (SEH) in ethyl acetate and the mixture was diluted with 50 ml of ether and 50 ml of isopropyl ether successively. The precipitate was collected by filtration to give 710 mg of the crude product 24, which was dissolved in 20 ml of water and chromatographed on a column using 50 ml of the packing in a PrepPAK/$C_{18}$ cartridge (Waters). The column was eluted with water and 10% methanol. The fractions containing the desired product were collected monitoring by HPLC and concentrated to 5 ml and lyophilized to give 182 mg (31%) of desired product, melting at 200° C. Estimated purity, 50% by HPLC.

IR: $\nu_{max}^{KBr}$ cm$^{-1}$ 1760, 1660, 1600, 1400, 1180, 1100.
UV: $\lambda_{max}^{phosphate\ buffer\ (pH\ 7)}$ nm($\epsilon$) 282 (5500).
NMR: $\delta^{D_2O}$ ppm 1.60 (3H, d, 6 Hz, —C—CH$_3$), 3.12 (1H, d, 18 Hz, 2—H), 3.48 (1H, d, 18 Hz, 2—H), 5.03 (1H, d, 4.5 Hz, 6—H), 5.62 (1H, d, 4.5 Hz, 7—H), 5.93 (1H, d, 10 Hz, vinyl—H), 5.2–5.8 (1H, m, vinyl—H), 7.41 (5H, s, phenyl—H).

Procedure 25

Benzhydryl
7β-[D-2-(t-Butoxycarbonylamino)-2-phenylacetamido]-3-[(Z)-3-chloro-1-propen-1-yl]-3-cephem-4-carboxylate (Compound 25)

To a solution of 2 g. (2 m mol) of 22 in 50 ml of chloroform was added 50 ml of water containing 2 ml (2 m mol) of N sodium hydroxide and the mixture was shaken for 3 minutes. The organic layer was separated and washed with water and a saturated NaCl solution successively. The dried chloroform solution was concentrated to 30 ml under reduced pressure. To the concentrate was added 2 ml of chloroacetaldehyde and the mixture was stirred at room temperature for one hour, washed with water, and subsequently with a saturated NaCl solution. The organic solution was dried and evaporated to dryness. The oily residue was chromtographed on a column of silica gel (Wako-gel C-200, 50 g) by eluting with chloroform. The desired fractions were collected and evaporated to dryness to give 534 mg of the crude product.

IR: $\nu_{max}^{KBr}$ cm$^{-1}$ 1780, 1710, 1660, 1500, 1490, 1360, 1240, 1210, 1150.

The structure of this sample was not confirmed because of its poor nmr spectrum.

Procedure 26

Sodium
7β-(D-2-amino-2-phenylacetamido)-3-[(Z)-3-chloro-1-propen-1-yl]-3-cephem-4-carboxylate (Compound 26, BB-S1066)

A mixture of 472 mg (0.7 m mol) of 25 and 1.5 ml of TFA was stirred at 10°–15° C. for 15 minutes and diluted with 30 ml of a mixture of ether and isopropyl ether (1:1) to afford 330 mg of pale yellow precipitate, which was collected by filtration. To a solution of the precipitate in 3 ml of methanol was added 2 ml (2 m mol) of SEH in ethyl acetate and the mixture was diluted with 50 ml of ethyl acetate. The resulting precipitate was collected by filtration and washed with ether to give 244 mg of a crude product. A solution of the crude product in 10 ml of water was chromatographed on a column using 50 ml of the packing in a PrepPAK-500/$C_{18}$ cartridge (Waters). The column was eluted with water and 10% methanol. The desired fractions of 10% methanol were combined and concentrated to 5 ml and lyophilized to give 60 mg of the solid product melting at 200° C. (grad. dec.).

IR: $\nu_{max}^{KBr}$ cm$^{-1}$ 1760, 1660, 1630, 1360, 1120, 1070.
UV: $\lambda_{max}^{phosphate\ buffer}$ nm($\epsilon$) 243 (12700), 200sh (4200).

Procedure 27

7β-(D(-)-2-Amino-2-phenylacetamido)-3-[(Z)-1-propen-1-yl]-3-cephem-4-carboxylic acid (Compound 24, BB-S 1065 zwitterion form)

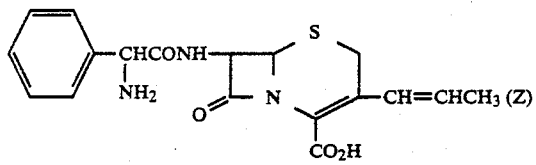

Diphenylmethyl 7-β-[D-2-(t-butoxycarbonylamino)-2-phenylacetamido]-3-(1-propenyl)-3-cephem-4-carboxylate (compound 23)1.5 g(2.34 m moles), was treated with 3 ml of trifluoroacetic acid and the mixture was stirred at room temperature for 20 min, and diluted with 100 ml of ether to give 1.15 g (96%) of the crude trifluoroacetate of BB-S 1065.

ir: $\nu_{max}$ (KBr) in cm$^{-1}$ 1760, 1670, 1200, 1130
uv: $\lambda_{max}$(pH 7 phosphate buffer) 283 nm ($\epsilon$: 8300)

The trifluoroacetate (1.1 g, 2.25 m moles) was dissolved in 20 ml of water and the solution was chromatographed on a column using 100 ml of the packing obtained from prepPAK/$C_{18}$ cartridge (Waters). The column was eluted with water, 10% methanol and 30% methanol. The eluate with 30% methanol was concentrated to 10 ml. The crystalline product was separated. The product was collected and washed with acetone and dried in vacuo over $P_2O_5$ to give 505 mg (46%) of pure BB-S 1065 (zwitterion form) melting at 180°–183° C.(dec.). Est'd purity 95%.

ir: $\nu_{max}$(KBr) in cm$^{-1}$ 1750, 1690, 1590, 1400, 1350.
uv: $\lambda_{max}$(pH 7 phosphate buffer) 282 nm ($\epsilon$: 8800).
nmr: $\delta$(D$_2$O+NaHCO$_3$) in ppm 1.58 (3H, d, J=6 Hz, C—CH$_3$), 3.3 (2H, d, 2—H), 5.03 (1H, d, J=4.5 Hz, 6—H), 5.20 (1H, s, CH—CO), 5.1–5.8 (1H, m, CH=C), 5.63 (1H, d, J=4.5 Hz, 7—H), 5.92 (1H, d, J=12 Hz, CH=C), 7.4 (5H, s, phenyl—H).

Procedure 28

D(−)-2-(t-Butoxycarbonylamino)-2-(3-chloro-4-hydroxyphenyl)acetic acid (Compound 28)

A mixture of 6 g (0.03 mole) of 3-chloro-4-hydroxyphenylglycine and 9.8 g (0.045 mole) of di-t-butyl dicarbonate in 120 ml of a 50% aqueous tetrahydrofuran (THF) solution containing 10 ml (0.071 mole) of triethylamine was stirred at room temperature for 3 hours. The mixture was concentrated to 60 ml and the concentrate was washed with ether. The aqueous layer was acidified with 6N hydrochloric acid and extracted with 200 ml of ether. The extract was washed with water and a saturated NaCl solution, dried on MgSO4, and evaporated to dryness to give 10 g of an oily residue, which did not solidify by attempted trituration with ether-n-hexane.

Procedure 29

Benzhydryl 7β-[D-2-(t-butoxycarbonylamino)-2-(3-chloro-4-hydroxyphenyl)acetamido]-3-chloromethyl-3-cephem-4-carboxylate (Compound 29)

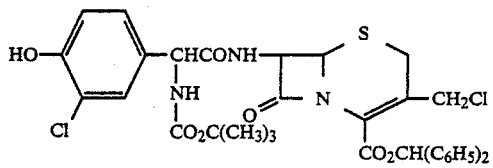

To a solution of 6.2 g (0.015 mole) of Compound 2 and 5.4 g (0.018 mole) of Compound 28 in 150 ml. of dry THF was added 3.7 g (0.018 mole) of DCC and the mixture was stirred at room temperature for one hour. Dicyclohexylurea, which separated during stirring, was removed by filtration and the filtrate was evaporated to dryness. The residue being extracted with 200 ml of ethyl acetate, the extract was washed with an aqueous NaHCO3 solution, water and a saturated NaCl solution, and dried with MgSO4. The filtrate was evaporated to dryness and the oily residue was chromatographed on a silica gel column (Wako gel C-200, 140 g) by eluting with toluene-ethyl acetate (b 10:1). The desired fractions were collected and evaporated to dryness to give 10 g of the product 29.

ir: $\nu_{max}$(KBr) in cm$^{-1}$ 1790, 1720, 1680, 1500, 1370, 1240, 1160.

Procedure 30

Benzhydryl 7β-[D-2-(t-Butoxycarbonylamino)-2-(3-chloro-4-hydroxyphenyl)acetamido]-3-(tripheylphosphonio)-methyl-3-cephem-4-carboxylate iodide (Compound 30)

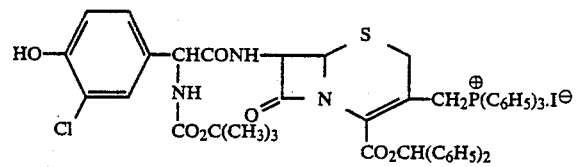

To a solution of 10 g (0.0143 mole) of Compound 29 in 100 ml of actone was added 11.2 g (0.075 mole) of sodium iodide and the mixture was stirred at room temperature for 30 min. The mixture was concentrated to 30 ml. To the concentrate was added 200 ml of ethyl acetate and the mixture was washed with an aqueous Na2S2O3 solution, water and a saturated NaCl solution, and dried with MgSO4. The ethyl acetate solution was filtered and the filtrate was concentrated to a half the volume. To the concentrate was added 3.9 g (0.015 mole) of triphenylphosphine and the mixture was stirred at room temperature for 2 hours. To the solution was added 300 ml of ether to separate a precipitate, which was collected by filtration and dried to give 9.2 g of the phosphonium iodide 30.

ir: $\nu_{max}$(KBr) in cm$^{-1}$ 1780, 1680, 1490, 1350, 1240, 1150.

Procedure 31

Benzhydryl 7β[D-2-(t-butoxycarbonylamino)-2-(3-chloro-4-hydroxyphenyl)acetamido]-3-[(Z)-1-propen-1-yl)-3-cephem-4-carboxylate (Compound 31)

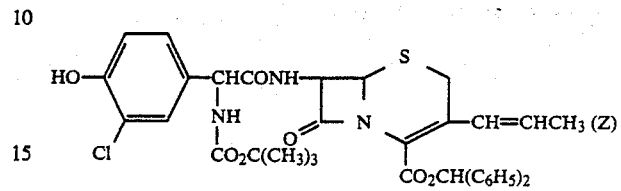

A solution of 9.5 g (9 m moles) of Compound 30 in 200 ml of chloroform was layered with a mixture of water (100 ml) and N NaOH (10 ml) and the mixture was shaken for 3 min. The organic layer was washed with water and a saturated NaCl solution, dried with MgSO4 and concentrated to about a half the volume. To the concentrate was added 20 ml of 90% acetaldehyde and the mixture was stirred at room temperature for 3 hours, treated with anhydrous MgSO4, and filtered. The filtrate was evaporated to dryness and the residue was chromatographed on Kiesel gel 60-(Merck, 120 g) by eluting with toluene-ethyl acetate (4:1). The desired fractions were collected and evaporated to dryness and the residue was triturated with a mixture of ether, isopropyl ether and n-hexane to give 1.33 g of the blocked product 31.

ir: $\nu_{max}$ (KBr) in cm$^{-1}$ 1770, 1700 1660, 1480, 1350, 1210, 1150.

Procedure 32

7β-[D-2-Amino-2-(3-chloro-4-hydroxyphenyl)acetamido]-3-[(Z)-1-propen-1-yl]-3-cephem-4-carboxylic acid (Compound 32, BMY28060)

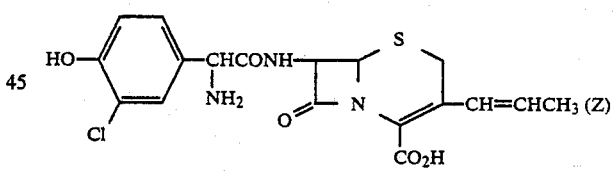

A mixture of 1.33 g (1.93 m moles) of Compound 31 and 3 ml of trifluoroacetic acid was stirred at room temperature for 30 min and the mixture was diluted with 50 ml of ether-isopropyl ether (1:1) to give 1.072 g of the crude trifluoroacetate of 32, which was chromatographed on a column packed with the packing of a prepPAK-C18 cartridge (Waters) (80 ml). The column was eluted with water and 10% methanol. The eluate with 10% methanol was concentrated to 10 ml of the volume to separate a crystalline precipitate, which was collected by filtration and washed with acetone and dried in vacuo over P2O5 to give 238 mg of 32 (95% pure) melting at 180°-185° C. (grad. dec.). The filtrate was concentrated to 5 ml and lyophilized to afford 154 mg of a second crop which was 80% pure by HPLC.

ir: $\nu_{max}$ (KBr) in cm$^{-1}$ 1760, 1680, 1570, 1410, 1390, 1350, 1290, 1270.

uv: $\lambda_{max}$ (pH7 phosphate buffer) in nm (ε) 232 (10000), 280 (10500).

nmr: δ (D₂O+NaHCO₃) in ppm 1,68 (3H, d, J=6 Hz, C=C—CH₃), 3.25 (1H, d, J=18 Hz, 2—H) 3.57 (1H, d, J=18 Hz, 2—H), 4.90 (1H, s, CH—CO), 5.18 (1H, d, J=4.5 Hz, 6—H), 5.72 (1H, d, J=4.5 Hz, 7—H), 5.5–5.9 (1H, m, CH=C), 5.97 (1H, d, J=12 Hz, CH=C), 7.02 (1H, d, J=8 Hz, phenyl—H), 7.30 (1H, d-d, J=8 & 1.5 Hz, phenyl-H), 7.50 (1H, d, J=1.5 Hz, phenyl—H).

Procedure 33

D(−)-2-(t-Butoxycarbonylamino)-2-(3,4-dihyroxyphenyl)acetic acid (33a) Mixture with Its 3-(and 4)-Mono-O-butoxycarbonyl Derivatives (33b).

A mixture of 3.66 g (0.02 mole) of 3,4-dihydroxyphenylglycine and 9.24 g (0.04 mole) of di-t-butyl dicarbonate in 120 ml of a 50% aqueous THF solution containing 10 ml (0.071 mole) of triethylamine was stirred at room temperature for 16 hours and the mixture was concentrated to 60 ml. The concentrate was washed with 100 ml of ether, acidified with N hydrochloric acid and extracted with ether (100×2 ml). The combined extracts were washed with water and a saturated NaCl solution, dried with MgSO₄ and evaporated in dryness to give 8 g of an oily residue which was a mixture of the desired 3,4-dihydroxyphenyl derivative and the 3- and 4-mono-O-BOC-protected derivatives (BOC refers to t-butoxy carbonyl).

Procedure 34

Benzhydryl 7β-[D(−)-2-(t-Butoxycarbonylamino)-2-(3,4-dihydroxyphenyl)acetamido]-3-chloromethyl-3-cephem-4-carboxylate (34a) and Mixture of its 3- (and 4-)Mono-O-butoxycarbionyl Derivatives (34b).

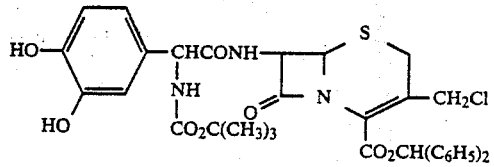

A mixture of 8 g (0.0193 mole) of Compound 2, 8 g of the mixed product of Procedure 33, and 4.12 g (0.02 mole) of DCC in 200 ml of dry THF was stirred at room temperature for one hour. The reaction mixture was evaporated to dryness. The residue was dissolved in 200 ml of ethyl acetate and insoluble material (dicyclohexylurea) was removed by filtration. The filtrate was washed with an aqueous NaHCO₃ solution, water and a saturated NaCl solution, dried with MgSO₄ and evaporated to dryness under reduced pressure. The oily residue was chromatographed on a silica gel column (Kiesel gel 60, 130 g) by eluting with toluene-ethyl acetate (5:1) and toluene-ethyl acetate (2:1). The eluate with toluene-ethyl acetate (5:1) was collected and evaporated to dryness to give 9.5 g of a mixture of the mono-O-BOC-N-BOC diprotected derivatives (34b). The eluate with toluene-ethyl acetate (2:1) was collected and evaporated to dryness to give 3 g of the 3,4-dihydroxyphenyl derivative (34a).

Compound 34a ir: ν$_{max}$ (KBr) in cm⁻¹ 1770, 1720, 1690, 1500, 1370, 1240, 1150.

nmr: δ (CDCl₃) in ppm 1,42 (9H, s, C—CH₃), 3.4 (2H, br-s, 2-H), 4.30 (2H, br-s, CH₂—Cl), 4.85 (1H, d, J=4.5 Hz, 6—H), 5.07 (1H, d, J=6 Hz, CH—NH), 5.74 (1H, d-d, J=9 & 4.5 Hz, 7—H), 6.6–6.9 (3H, m, phenyl—H), 6.93 (1H, s, CHPh), 7.3 (10H, s, phenyl—H).

Mixture 34b ir: ν$_{max}$ (KBr) in cm⁻¹ 1770, 1720, 1690, 1500, 1370, 1240, 1150.

nmr: δ (CDCl₃) in ppm 1,42 (9H, s, C—CH₃), 1.55 (9H, s, C—CH₃), 3.4 (2H, br-s, 2—H), 4.35 (2H, br-s, CH₂—Cl), 6.9–7.1 (4H, m, CHPh & phenyl—H), 7.3 (10H, s, phenyl—H).

Procedure 35

Benzhydryl 7β-[D(−)-2-(t-Butoxycarbonylamino)-2-(3,4-dihydroxyphenyl)acetaido]-3-triphenylphosphoniomethyl-3-cephem-4-carboxylate Iodide (35a).

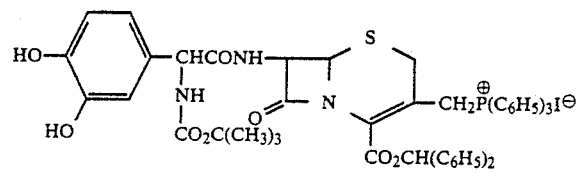

A mixture of 3 g (4.4 m moles) of 34a and 3.3 g (22 m moles) of sodium iodide in 50 ml of acetone was stirred at room temperature for 30 min and the mixture was concentrated to dryness. The residue was extracted with 100 ml of ethyl acetate and the extract was washed with an aqueous Na₂S₂O₃ solution, water and a saturated NaCl solution. After drying with MgSO₄ the extract was concentrated to 60 ml. To the concentrate was added 1.4 g (5.3 m moles) of triphenylphosphine and the mixture was stirred at room temperature for one hour. To the mixture was added 100 ml of ether to separate a precipitate, which was collected by filtration and washed with ether to give 3.2 g (70%) of the phosphonium iodide (35a).

ir: ν$_{max}$ (KBr) in cm⁻¹ 1780, 1680, 1480, 1430, 1360, 1240, 1150.

By a similar procedure, 9.5 g (12 m moles) of the mixture of mono-O-BOC-protected derivatives (34b) was allowed to react with sodium iodide and subsequently with triphenylphosphine to give 10.7 g (77%) of a mixture of the corresponding mono-O-BOC-N-BOC triphenyphosphoniomethyl derivatives (35b).

ir: ν$_{max}$ (KBr) in cm⁻¹ 1770, 1720, 1680, 1480, 1430, 1360, 1240, 1140.

Procedure 36

Benzhydryl 7β-[D(−)-2-(t-Butoxycarbonylamino)-2-(3,4-dihydroxyphenyl)acetamido]-3-[(Z)-1-propen-1-yl]-3-cephem-4-carboxylate (Compound 36a)

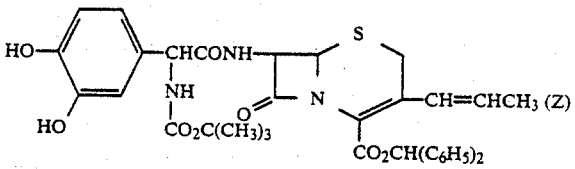

To a stirred solution of 3.15 g (3 m moles) of Compound 35a and 10 ml of acetaldehyde in 50 ml of chloroform was added dropwise 8 ml (4 m moles) of 0.5N sodium hydroxide over a period of 10 min and the mixture was stirred at room temperature for one hour. The reaction mixture was washed with water and a saturated NaCl solution, dried with MgSO₄ and evaporated under reduced pressure. The oily residue was chromatographed on a silica gel column (Wako gel C-200, 60 g), which was eluted with chloroform (2 L) and 2% methanol in chloroform under monitoring by TLC (chloroform:methanol=10:1). The desired fractions from the 2% methanol eluate were collected and evaporated to dryness to give 0.8 g (40%) of the propenyl derivative 36a.

nmr: δ (CDCl₃) in ppm 1.28 (3H, d, J=6 Hz, C—CH₃), 1.42 (9H, s, C—CH₃), 3.25 (2H, s, 2—H), 4.92 (1H, d, J=4.5 Hz, 6—H), 5.08 (1H, d, J=6 Hz, CH—NH), 5.3–5.8 (1H, m, CH=C), 5.80 (1H, d, J=4.5 Hz, 7—H), 6.04 (1H, d, J=11 Hz, CH=C), 6.70 (2H, s, phenyl—H), 6.82 (1H, s, phenyl—H), 6.92 (1H, s, CHPh), 7.3 (10H, s, phenyl—H).

By a similar procedure to that described above, 10.5 g (9.3 m moles) of the mixture of the 3- and 4-O-BOC-N-BOC diprotected derivatives 35b was allowed to react with acetaldehyde to give, 3.3 g (46%) of the corresponding 3-propenyl derivative 36b.

ir: ν$_{max}$ (KBr) in cm⁻¹ 1770, 1700, 1500, 1370, 1240, 1150.

nmr: δ (CDCl₃) in ppm 1.4 (9H, s, C—CH₃), 1.55 (9H, s, C—CH₃), 3.25 (2H, s, 2—H), 6.07 (1H, d, J—11 Hz, CH=C), 6.9–7.1 (4H, m, CH—Ph & phenyl—H), 7.3–7.5 (10H, m, phenyl—H).

Procedure 37

7β-[D(−)-2-Amino-2-(3,4-dihydroxyphenyl-)acetamido]-3-[(Z)-1-propen-1-yl]-3-cephem-4-carboxylic Acid (Compound 37, BMY-28068).

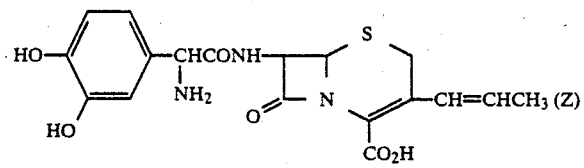

A mixture of 0.8 g (1.2 m moles) of compound 36a, 0.8 ml of anisole and 3 ml of trifluoroacetic acid was stirred at room temperature for 5 min and diluted with 25 ml of ether and 25 ml of isopropyl ether. The resulting precipitate was collected by filtration and washed with isopropyl ether to give 557 mg of the crude trifluoroacetate salt of Compound 37. A solution of the crude product in 10 ml of water was purified by column chromatography using 100 ml of the packing of a prep-PAK-C₁₈ cartridge (Waters) and the column was eluted with water and 5% methanol successively. The 5% methanol eluate containing the desired product was concentrated to 5 ml and lyophilized to give 231 mg (47%) of Compound 37 (zwitterion form, 90% pure). M.p. 200° C. (grad. dec.).

ir: ν$_{max}$ in cm⁻¹ 1760, 1690, 1580, 1530, 1400, 1360, 1290, 1270.

uv: λ$_{max}$ (pH7 phosphate buffer) in nm (ε) 233 (9200), 281 (11000)

nmr: δ (D₂O) in ppm 1.68 (3H, d, J=6 Hz, C—CH₃), 3.26 (1H, d, J=18 Hz, 2—H), 3.58 (1H, d, J=18 Hz, 2—H), 5.18 (1H, s, CHNH), 5.22 (1H, d, J=4.5 Hz, 6—H), 5.5–5.9 (2H, m, CH=C & 7—H), 5.97 (1H, d, J=11 Hz, CH=C), 7.05 (3H, m, phenyl—H).

According to a similar procedure, 3.3 g (4.3 m moles) of the N,O-di-t-BOC-protected derivative mixture 36b gave 1.3 g (75%) of Compound 37 as the zwitterion form (90% pure), which gave the spectral data identical with those given above.

Procedure 38

D(−)-2-(t-Butoxycarbonylamino)-2-(4-hydroxy-3-methoxyphenyl)acetic Acid (Compound 38)

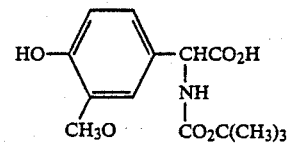

A mixture of 2.96 g (0.015 mole) of D(−)-2-amino-2-(4-hydroxy-3-methoxyphenyl)acetic acid and 3.6 g (0.0165 mole) of di-t-butyl dicarbonate in 100 ml of 50% aqueous THF containing 4.2 ml (0.03 mole) of triethylamine was stirred at room temperature for 16 hours and the reaction mixture was concentrated to 50 ml. The concentrate was washed with 50 ml of ether, acidified with N hydrochloric acid and extracted twice with ether (100×2 ml). The combined extracts were washed with water and a saturated NaCl solution. The dried extracts were evaporated to dryness to give 4.38 g of compound 38 as foamy solid.

nmr: δ (CDCl₃) in ppm 1.4 (9H, s, —C—CH₃), 3.8 (3H, s, OCH₃), 5.15 (1H, d, J=6 Hz CH—NH), 6.85 (3H, s, phenyl—H).

Procedure 39

Benzhydryl 7β-[D(−)-2-(t-Butoxycarbonylamino)-2-(4-hydroxy-3-methoxyphenyl)-acetamido]-3-chloromethyl-3-cephem-4-carboxylate (Compound 39)

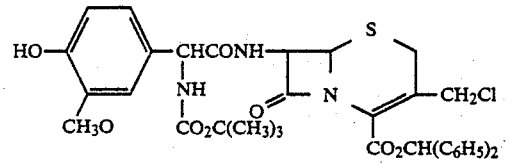

A mixture of 4.3 g of Compound 38, 5 g (0.012 mole) of Compound 2, and 3 g (0.015 mole) of DCC in 150 ml of dry THF was stirred at room temperature for 2 hours. The precipitated urea was removed by filtration and the filtrate was evaporated to dryness. A solution of the residue in 200 ml of ethyl acetate was washed with an aqueous NaHCO₃ solution, water, and a saturated NaCl solution, dried with MgSO₄ and evaporated to dryness. The oily residue was chromatographed on a silica gel column (Kiesel gel 60, 100 g) which was eluted with toluene-ethyl acetate (4:1) under monitoring by TLC [toluene-ethyl acetate (1:1) or chloroform-methanol (50:1)]. The desired fractions were collected and evaporated to dryness to give 7 g of the desired 3-chloromethyl cephem, Compound 39, as a foamy solid.

nmr: δ in ppm 1.4 (9H, s, C—CH₃), 3.45 (2H, br-s, 2—H), 3.83 (3H, s, OCH₃), 4.32 (2H, s, —CH₂Cl), 4.92 (1H, d, J=4.5 Hz, 6—H), 5.13 (1H, d, J=6 Hz CH—NH), 5.65 (1H, d, J=6 Hz, NH), 5.80 (1H, d-d, J=8 & 4.5 Hz, 7—H), 6.85 (3H, s, phenyl—H), 6.95 (1H, s CH—Ph), 7.2–7.5 (10—H, m. phenyl—H).

Procedure 40

Benzhydryl 7β-[D(−)-2-(t-Butoxycarbonylamino)-2-(4-hydroxy-3-methoxyphenyl)-acetamido]-3-triphenylphosphoniomethyl-3-cephem-4-carboxylate Iodide (Compound 40)

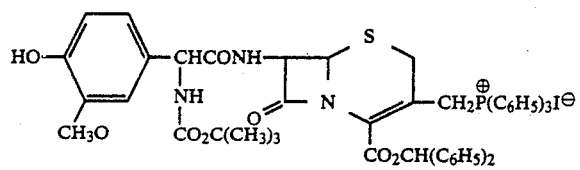

A mixture of 7 g (0.01 mole) of Compound 39, and 7.5 g (0.05 mole) of sodium iodide in 100 ml of acetone was stirred at room temperature for 30 min and evaporated to dryness. A solution of the residue in 200 ml of ethyl acetate was washed with an aqueous $Na_2S_2O_3$ solution, water and a saturated NaCl solution, dried with $MgSO_4$ and concentrated to 100 ml. To the concentrate was added 3.1 g (0.012 mole) of triphenylphosphine and the mixture was stirred at room temperature for one hour. To the reaction mixture was added 100 ml of ether and the separated solid was collected by filtration, washed with ether and dried to give 5.8 g the triphenylphosphonium derivative Compound 40. The ethereal filtrate was concentrated to 10 ml and to the concentrate was added 300 ml of ether to give 0.9 g of the product as a second crop. The total yield was 6.7 g.

Procedure 41

Benzhydryl 7β-[D-(−)-2-(t-Butoxycarbonylamino)-2-(4-hydroxy-3-methoxyphenyl-acetamido]-3-[(Z)-1-propen-1-yl]-3-cephem-4-carboxylate (Compound 41)

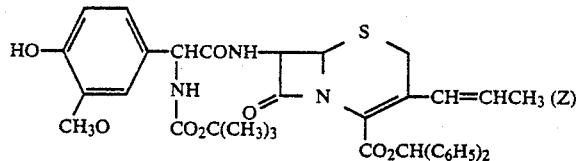

To a stirred mixture of 5.8 g (5.5 m moles) of Compound 40 and 10 ml of 90% acetaldehyde in 100 ml of chloroform was added dropwise 11 ml (5.5 m moles) of 0.5N sodium hydroxide over a period of 25 min and the mixture was stirred at room temperature for 2 hours. The reaction mixture was washed with water, then with a saturated NaCl solution, dried with $MgSO_4$, and evaporated to dryness. The oily residue was chromatographed on a silica gel column (Kiesel gel 60, 130 g) by eluting with a mixture of toluene and ethyl acetate [the ratio was changed stepwise; 4:1 (1.3 L), 3:1 (1.1 L), 2:1 (1.0 L) and the eluate was collected in 20-ml fraction. Fractions No. 26 through fraction No. 59 were combined and evaporated to dryness to give 830 mg of the desired 3-propenyl derivative Compound 41 as a foamy solid.

nmr of 41: δ (CDCl₃) in ppm, 1.35 (3H, d, =CH—CH₃), 1.4 (9H, s, C—CH₃) 3.85 (3H, s, O—CH₃), 6.07 (1H, d, J=11 Hz, —CH=C).

Procedure 42

7β-[D(−)-2-Amino-2-(4-hydroxy-3-methoxyphenyl)acetamido]-3-[(Z)-1-propen-1-yl]-3-cephem-4-carboxylic Acid (Compound 42, BMY 28097)

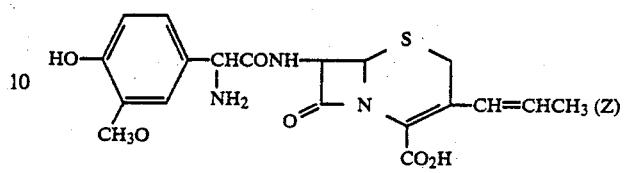

A mixture of 830 mg (1.2 m moles) of Compound 41, 0.5 ml of anisole and 2 ml of trifluoroacetic acid was stirred at room temperature for 5 min and the mixture was diluted with 30 ml of ether and 30 ml of isopropyl ether. The resulting precipitate was collected by filtration, washed with isopropyl ether and dried to give 437 mg of the crude trifluoroacetate of Compound 42. The crude product was chromatographed on a column packed with 100 ml of the packing of a prepPAK-C₁₈ cartridge column (Waters), which was eluted with water and 5% methanol. The eluate with 5% methanol was concentrated to 5 ml and lyophilized to give 225 mg of Compound 42 (zwitterion, 90% pure). M.p. 176°–180° C. (dec.).

ir: $\nu_{max}$ in cm$^{-1}$ 1760, 1690, 1590, 1530, 1400, 1360, 1280.

uv: $\lambda_{max}$ (pH 7 phosphate buffer) in nm (ε) 235 (10000), 280 (11000).

nmr: δ (D₂O) in ppm 1.68 (3H, d, J=6 Hz, C—CH₃), 3.25 (1H, d, J=18 Hz, 2—H), 3.57 (1H, d, J=18 Hz, 2—H), 4.01 (3H, s, OCH₃), 5.10 (1H, s, CH—CO), 5.19 (1H, d, J=4.5 Hz, 6—H), 5.78 (1H, d, J=4.5 Hz, 7—H), 5.5–5.9 (1H, m, CH=C), 5.98 (1H, d, J=11 Hz, CH=C), 7.07 (2H, phenyl—H), 7.17 (1H, br-s, phenyl—H).

HPLC: retention time 9.3 min. (0.02M acetate buffer (pH 4) containing 15% acetontrile).

Procedure 43

Isolation of Compound 42 from the Urine of Rats fed Compound 37

Six male Wistar rats (400–600 g) were placed in steel metabolic cages after the oral administration of Compound 37 at the dose of 100 mg/kg and urine was collected over a period of 24 hours. The rats were fed their regular diet and given water during the experiment. The following table shows the volume of urine collected from time to time.

| | 0–2 hr | 2–4 hr | 4–6 hr | 6–24 hr | Total |
|---|---|---|---|---|---|
| Urine volume (ml) | 18 | 19.5 | 13 | 42 | 92.5 |

The urine (ca. 90 ml) was adjusted to pH 3 with N hydrochloric acid and filtered to remove a precipitate. The filtrate was chromatographed on a column packed with 300 ml of HP-20 by eluting with 2 L of water and 2 L of 30% methanol under monitirong with HPLC. The fractions containing the bioactive components of the 30% methanol eluate were collected, concentrated to 10 ml and lyophilized to give 390 mg of brown solid. A solution of the solid in 20 ml of water was chromatographed on a column packed with 200 ml of the packing of a prepPAK-$C_{18}$ cartridge (Waters) by eluting with water, 5% methanol, and 10% methanol, successively. The first half of the 5% methanol eluate was concentrated to 5 ml and lyophilized to give 44 mg of Compound 37 (70% pure) containing impurities derived from urine. The second half of the 5% methanol eluate was concentrated to 5 ml and lyophilized to give 36 mg of product, which was a mixture of Compound 37, Compound 42, and impurities derived from urine. The eluate with 10% methanol (ca. 600 ml) was concentrated to 5 ml and lyophilized to give 38 mg of Compound 42 (70% pure by HPLC), which was rechromatographed on a column of the same packing as above (40 ml) by eluting with water, 5% methanol and 10% methanol. The desired fractions eluted with 10% methanol were combined and concentrated to 5 ml and lyophilized to give 16 mg of Compound 42 which was 90% pure by HPLC (0.02M acetate buffer (pH 4)-acetonitrile (85:15). M.p. 180° C. (grad. dec.).

ir: $\nu_{max}$ (KBr) in cm$^{-1}$ 1760, 1690, 1590, 1530, 1400, 1360, 1280.

uv: $\lambda_{max}$ (pH 7 phosphate buffer) in nm ($\epsilon$) 233 (8200), 280 (8800).

nmr: $\delta$ (D$_2$O) in ppm 1.68 (3H, d, J=6 Hz, —C—CH$_3$), 3.26 (1H, d, J=18 Hz, 2—H), 3.58 (1H, d, J=18 Hz, 2—H), 4.01 (3H, s, OCH$_3$), 5.12 (1H, s, CH—CO), 5.21 (1H, d, J=4.5 Hz, 6—H), 5.78 (1H, d, J=4.5 Hz, 7—H), 5.5-5.9 (1H, m, CH=C—), 5.98 (1H, d, J=11 Hz, CH=C—), 7.07 (2H, s, phenyl—H), 7.17 (1H, br-s, phenyl—H).

The structure of the metabolite was established as 7β-[D(—)-2-amino-2-(4-hydroxy-3-methoxyphenyl)acetamido]-3-[(Z)-1-propen-1-yl]-3-cephem-4-carboxylic acid by comparison (nmr, ir, uv, HPLC) with the Compound 42 prepared by Procedure 38-42.

What is claimed is:

1. A compound selected from the group consisting of those having the formula

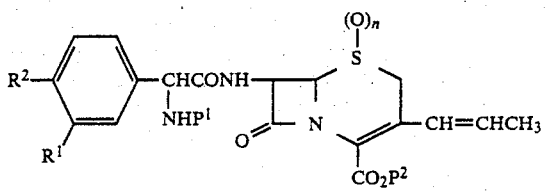

and the Z-configuration about the exocyclic double bond wherein n is the integer 0, or 1, $R^1$ is hydrogen, $OP^3$, lower alkoxy, or halogen, $P^1$, $P^2$, and $P^3$ are hydrogen atoms or conventional protecting groups used in cephalosporin chemistry respectively with amino, carboxy, and hydroxy groups, $R^2$ is hydrogen, or $OP^3$, the acid addition salts of the foregoing substances wherein $P^1$, is hydrogen, and the metal salts of the foregoing substances wherein $P^2$ is hydrogen wherein at least one of $P^1$, $P^2$, and $P^3$ is a said protecting group when n is zero.

2. The compound of claim 1 wherein n is 0, and at least one of $P^1$, $P^2$, and $P^3$ is a conventional protecting group.

3. The compound of claim 2 wherein $P^1$, and $P^3$ when protecting groups are independently selected from the group consisting of trityl, chloroacetyl, formyl, trichloroethoxycarbonyl, and t-butoxycarbonyl, benzyloxycarbonyl, and $P^2$ when a protecting group is selected from the group consisting of benzyl, p-methoxybenzyl, p-nitrobenzyl, diphenylmethyl, t-butyl, and 2,2,2-trichloroethyl.

4. The compound of claim 2 known by the chemical name diphenylmethyl 7β-[2-(t-butoxycarbonylamino)-2-(4-hydroxyphenyl)acetamido[3-[(Z)-1-propen-1-yl]ceph-3-em-4-carboxylate.

* * * * *